United States Patent
Federici et al.

(10) Patent No.: US 7,459,687 B2
(45) Date of Patent: Dec. 2, 2008

(54) NON-LINEAR TERAHERTZ SPECTROSCOPY FOR DEFECT DENSITY IDENTIFICATION IN HIGH K DIELECTRIC FILMS

(75) Inventors: John Francis Federici, Westfield, NJ (US); Haim Grebel, Livingston, NJ (US); Hakan Altan, New York, NY (US)

(73) Assignee: New Jersey Institute of Technology, Newark, NJ (US)

(*) Notice: Subject to any disclaimer, the term of this patent is extended or adjusted under 35 U.S.C. 154(b) by 0 days.

(21) Appl. No.: 11/697,357

(22) Filed: Apr. 6, 2007

(65) Prior Publication Data

US 2007/0235650 A1    Oct. 11, 2007

Related U.S. Application Data

(60) Provisional application No. 60/789,683, filed on Apr. 6, 2006.

(51) Int. Cl.
*G01J 5/02* (2006.01)
(52) U.S. Cl. .................................. 250/341.8
(58) Field of Classification Search .... 250/341.1–341.8
See application file for complete search history.

(56) References Cited

U.S. PATENT DOCUMENTS

| | | | | |
|---|---|---|---|---|
| 4,821,302 A | * | 4/1989 | Whitlock et al. | 378/73 |
| 5,944,193 A | * | 8/1999 | Shimizu | 206/710 |
| 6,734,974 B2 | * | 5/2004 | Jiang et al. | 356/432 |
| 2001/0019401 A1 | * | 9/2001 | Irie et al. | 355/53 |
| 2001/0038074 A1 | * | 11/2001 | Zhang et al. | 250/341.8 |
| 2003/0155512 A1 | * | 8/2003 | Arnone et al. | 250/341.1 |
| 2005/0098728 A1 | * | 5/2005 | Alfano et al. | 250/341.8 |
| 2005/0230625 A1 | * | 10/2005 | Zhang et al. | 250/341.1 |
| 2005/0253071 A1 | * | 11/2005 | Ferguson et al. | 250/341.1 |

OTHER PUBLICATIONS

Abrahamson J., "Modeling Alternative High Dielectric Constant Thin Films," REU 2004 Summer Program, Advanced Materials Research Laboratory, University of Illinois at Chicago (2004).
H. Altan, A. Sengupta, D. Pham, H. Grebel and J.F. Federici, "Characteristics of HfO2 and SiO2 on p-type Silicon wafers using THz spectroscopy," Semicond. Sci. Tech., 22, 457-463, 2007 [Appeared in Virtual Journal of THz Science and Technology, May 2007].

(Continued)

*Primary Examiner*—David P. Porta
*Assistant Examiner*—Kiho Kim
(74) *Attorney, Agent, or Firm*—Timothy X. Gibson, Esq.; Gibson & Dernier LLP

(57) ABSTRACT

Methods to infer the density of defects in high κ dielectric films in a non-contact, non-invasive and non-destructive manner. THz radiation is employed to measure the change in electrical conductivity of the films before and after illumination with visible light, where the visible light photoionizes the defects thereby changing the electrical conductivity and changing the transmission (or reflection) of THz radiation from the films. The disclosed techniques can be employed to make measurements as soon as wafers are fabricated. The technology is applicable to wafers of any size.

19 Claims, 26 Drawing Sheets

OTHER PUBLICATIONS

Beard, M.C., and Schmuttenmaer, C.A., "Using the Finite-Difference Time-Domain Pulse Propagation Method to Simulate Time-Resolved THz Experiments" J. Chem. Phys., 114, 2903 (2001).

Beard, M.C., Turner, G.M., and Schmuttenmaer, C.A., "Sub-picosecond carrier dynamics in low-temperature grown GaAs as measured by time-resolved THz spectroscopy." J. Appl. Phys., 90, 5915-5923 (2001).

Cai, Y., "Enhanced terahertz pulse generation and detection using electric-field singularities in photo-conducting antennas," Dissertation, NJIT, Newark, NJ (1998).

Chau R.S., "Intel's breakthrough in High K gate dielectric drives Moore's law well into the future," Intel Technological Magazine, 1, 3-10 (2004).

Grandqvist C.G. and Hunderi O., "Optical properties of ultrafine gold particles," Phys. Rev. B, 16, 3513-3534 (1977).

Grunthaner F.J. and Grunthaner P.J., "Chemical and electronic structure of the Si/SiO2 interface," Mater. Sci. Rep. 1, 65-160 (1986) (abstract only).

Kalnin J.R. and Kotomin E., "Modified Maxwell-Garnett and Lorentz-Lorentz equations for the effective transport coefficients in inhomogeneous media," J. Phys. A: Math. Gen., 31, 7227-7234 (1998).

Kersting, R., Unterrainer, K., Strasser, G., Kaufmann, H.F., and Gornik, E., "Few cycle THz emission from cold plasma oscillations," Phys. Rev. Lett., 79 (16), 3038-3041 (1997).

Lee B.J. and Zhang B.M., "Development of experimentally validated optical property models for silicon and related materials," Proc. Of 11th IEEE International Conference on Advanced Thermal Processing of Semiconductors, RTP 2003, 143-150 (2003).

Levy O. and Stroud D., "Maxwell-Garnett theory for mixtures of anisotropic inclusions: Application to conducting polymers," Phys. Rev. B., 56, 8035-8056 (1997).

Lin, Y.-S., Puthenkovilakam, R., and Chang, J.P., "Dielectric property and thermal stability of HfO2 on silicon," Appl. Phys. Lett. 81, 2041-2043 (2002).

McLaughlin, R., Corchia, A., Johnston, M.B., Chen, Q., Ciesla, C.M., Arnone, D.D., Jones, G.A.C., Linfield, E.H., Davies, A.G., and Pepper, M., "Enhanced coherent terahertz emission from indium arsenide in the presence of a magnetic field," Appl. Phys. Lett., 76 (15), 2038-2040 (2000).

Mitrofanov, O., "Near-Field Imaging with THz pulses," Dissertation, NJIT, Newark, NJ (2001).

Muller D.A., Sorsch T., Moccio S., Baumann F.H., Evans-Lutterodt K. and Timp G., "The electronic structure at the atomic scale of ultrathin gate oxides," Nature, 399, 758-762 (1999).

Nemec, H., "Application of methods in time-domain terahertz spectroscopy for investigation of ultrafast dynamics in condensed matters," Diploma Thesis, Charles University in Prague, Czech Republic (2002).

Optical properties of Silicon. Site details optical properties of Silicon at different wavelengths. Retrieved Feb. 17, 2006 from http://www.virginiasemi.com/pdf/Optical20Properties20of20Silicon71502.pdf.

Perera A.G.U, Shen W.Z., Mallard W.C., Tanner M.O. and Wang K.L., "Far infrared free hole absorption in epitaxial silicon films for homojunction detectors," Appl. Phys. Lett., 71, 515-517 (1997).

Philip H.R. and Ehrenrich H., "Optical properties of semiconductors," Phys. Rev., 129, 1550-1560 (1963).

Planken, P.C.M., Nuss, M.C., Brener, I., and Goossen, K.W., "Terahertz emission in single quantum wells after coherent excitation of light hole and heavy hole excitons," Phys. Rev. Lett., 69 (26), 3800-3803 (1992).

Semiconductor International, Reed Electronics Group. Site details properties of deep UV photoresist under different conditions. Retrieved Oct. 31, 2004 from http://www.reed-electronics.com/semiconductor/article/CA41503.pdf.

Van Kranendonk J. and Sipe J.E., "Foundations of the macroscopic electromagnetic theory," Prog. Opt., 15, 246-350 (1977).

Wilk G.D., Wallace R.M. and Anthony J.M., "High K gate dielectrics: current status and materials properties considerations," J. Appl. Phys., 89, 5243-5275 (2001).

Zhang, X.C., and Auston, D.H., "Optoelectronic measurement of semiconductor surfaces and interfaces with femtosecond optics," J. Appl. Phys., 71 (1), 326-338 (1992).

Zhang, X.C., Hu, B.B., Darrow, J.T., and Auston, D.H., "Generation of femtosecond electromagnetic pulses from semiconductor surfaces," Appl. Phys. Lett., 56 (11), 1011-1013 (1990).

Zielbauer J. and Wegener M., "Ultrafast optical pump THz-probe spectroscopy on silicon," Appl. Phys. Lett., 68, 1223-1225 (1996).

Zukic M., Torr D.G., Span J.F. and Torr M.R., "Vacuum ultraviolet thin films. 1: Optical Constants of HaFBaF2, CaF2, LaF3, MgF2, AI203, HfO2 and SiO2 thin films," Appl. Opt., 29, 4284 (1990).

* cited by examiner

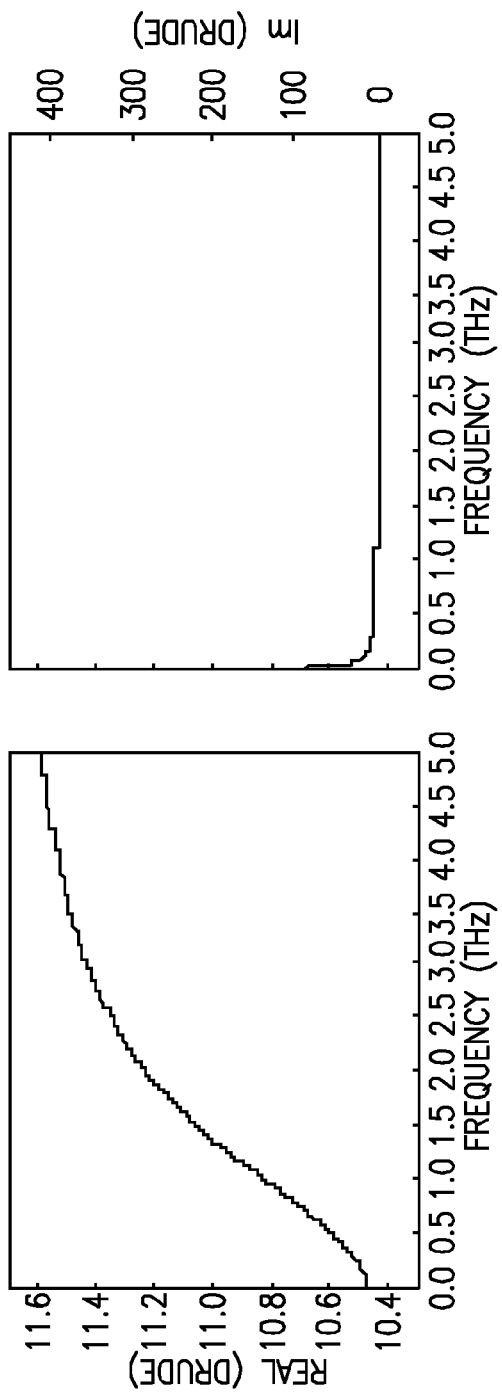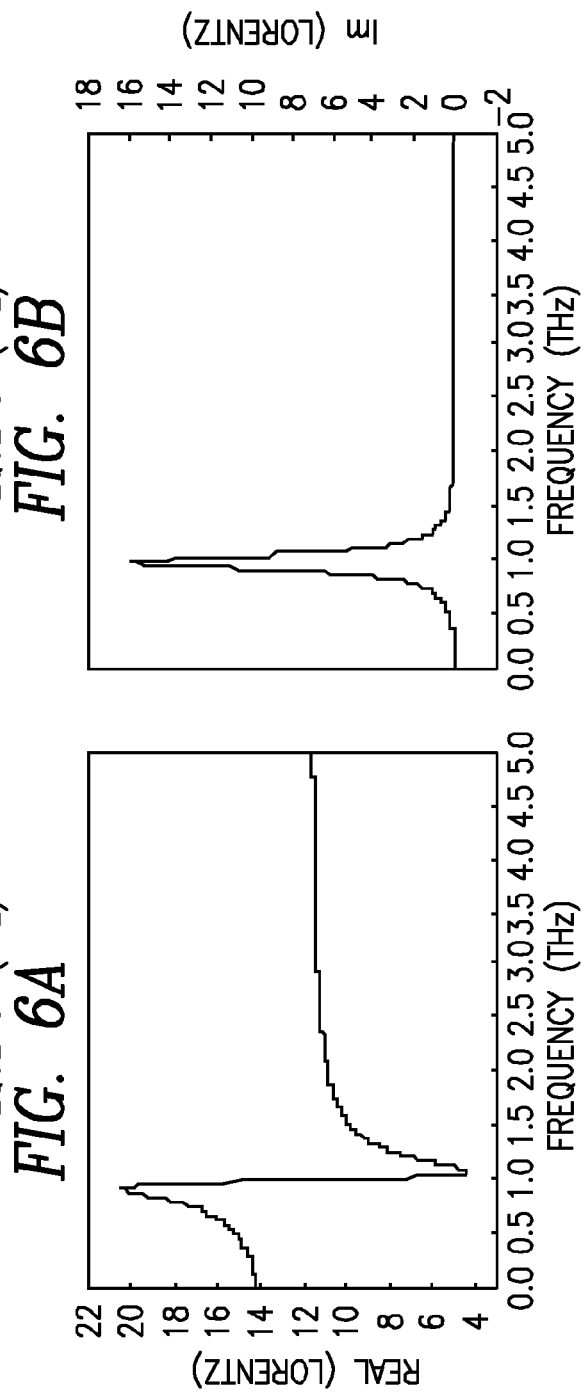
FIG. 6A  FIG. 6B  FIG. 6C  FIG. 6D

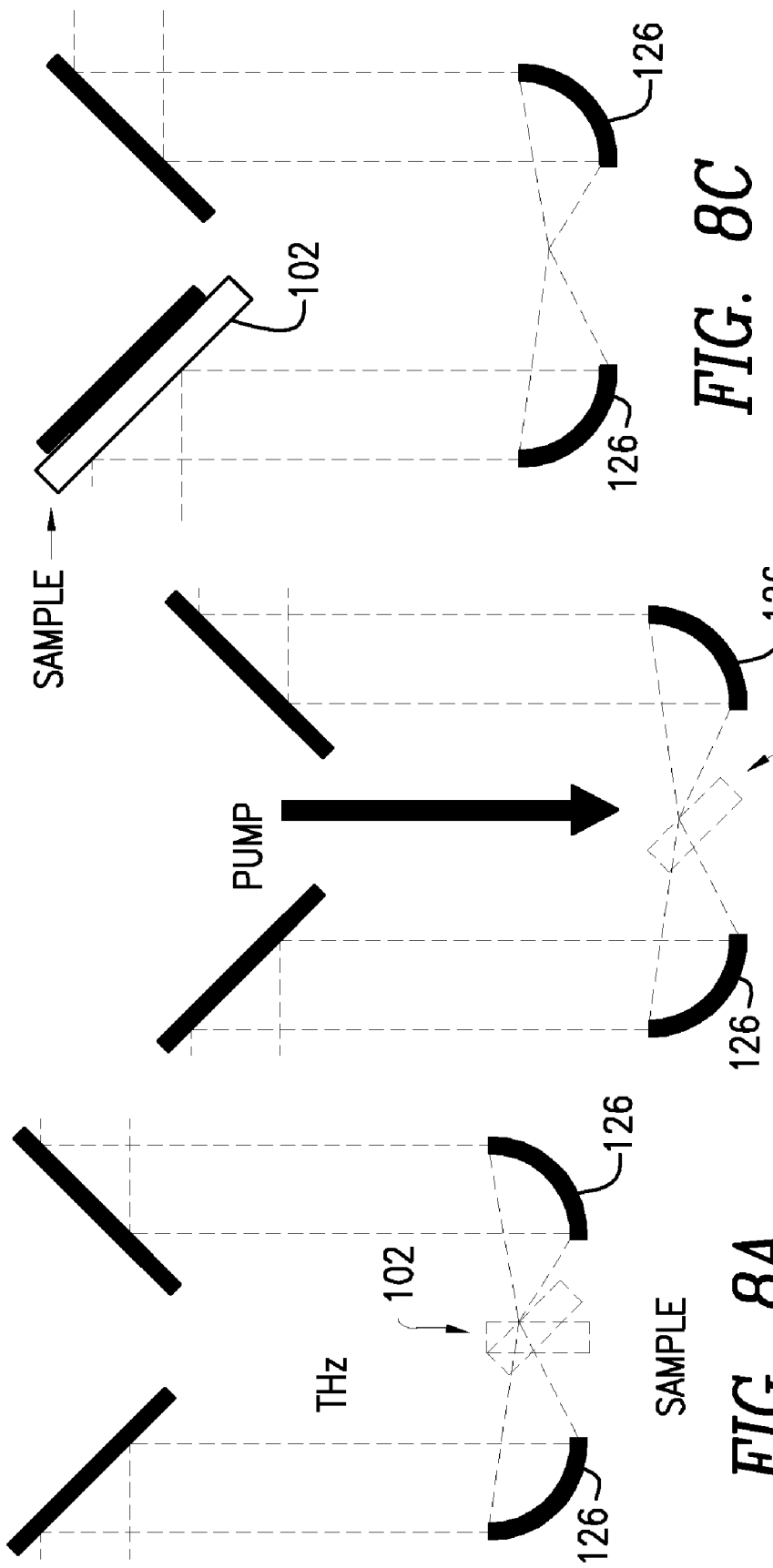

NON-LINEAR TERAHERTZ SPECTROSCOPY FOR DEFECT DENSITY IDENTIFICATION IN HIGH K DIELECTRIC FILMS

CROSS-REFERENCE TO RELATED APPLICATIONS

This Application claims the benefit of U.S. Provisional Patent Application Ser. No. 60/789,683, filed Apr. 6, 2006, entitled "Non-Linear Terahertz Spectroscopy for Defect Density Identification in High K Dielectric Films", the entire disclosure of which is incorporated by reference herein.

BACKGROUND OF THE INVENTION

1. Field of the Invention

This invention relates to a method and apparatus for performing terahertz (THz) spectroscopy and, more particularly, for optically pumping and THz probing a sample object under test by a non-linear technique.

2. Description of the Related Art

Over the years, the trend towards smaller scales in Metal-Oxide Semiconductor Field-Effect Transistors (MOSFETs) and other CMOS based technologies has brought about substantial improvements in devices performance. However, the silicon-based microelectronics industry is rapidly approaching the point where device performance is compromised by feature size. Specifically, the gate dielectric based on $SiO_2$ scaled to a node size of 90 nm will not insulate well enough, thereby leading to gate leakage. Current MOSFET technology with 1.3 nm thick $SiO_2$ as the gate dielectric material portrays high gate leakage and reduced drive currents, thus limiting the operation range of the device and also increasing power consumption. Gate leakage currents however, can be minimized by using other dielectric materials with higher permittivity values than their $SiO_2$, counterpart. These other dielectric materials exhibit smaller electric fields under the same bias conditions than does $SiO_2$.

$SiO_2$ has been the industry workhorse for many years. It exhibits extremely low defects when grown on Si substrate and therefore has little effect on the performance of the device. Despite many efforts, a high-κ dielectric material that provides as suitable an interface with silicon as with $SiO_2$ has not been found. However, manufacturing processes that incorporate dielectric composites such as hafnium-silicate ($H_xSiO$) or plasma-nitride hafnium-silicate ($H_xSiON$) have provided improved oxide interfaces for device manufacturing. Among the factors that contribute to a poor interface between the oxide and the Si substrate are thermodynamic stability with silicon at elevated temperatures, the dielectric constant, and the silicon conduction band offset. Herein, high-κ dielectric material refers to material having a dielectric constant higher than that of $SiO_2$. More specifically, high-κ dielectric material may have a dielectric constant higher than 3.9.

A large number of gate dielectric materials have been examined during the past few years. Films such as $HfO_2$ $HfSi_xO_y$, have gained much attention for their potential applications in advanced microelectronics. Various methods have been developed to deposit these high-κ dielectric materials, such as chemical vapor deposition, physical vapor deposition, and ion-assisted deposition. Hf-based high-κ dielectrics have become a very promising candidate to replace $SiO_2$ in MOSFETs due to their adequate band-gaps and conduction-band offsets. (See, Lin, Y.-S., Puthenkovilakam, R., and Chang, J. P., "Dielectric property and thermal stability of HfO2 on silicon," Appl. Phys. Lett. 81, 2041-2043 (2002) and Robertson J 2000 J. Vac. Sci. Technol. B 18 1785). A dielectric constant around 25, thermodynamic stability with Si up to 950° C., and a conduction band offset of 1.5 eV allow it (Hf-based dielectric material) to offer a sufficient barrier against electron tunneling with an equivalent oxide thickness (EOT) as small as 10 angstroms. If the capacitor dielectric is $SiO_2$, a capacitance density of 34.5 fF/$\mu m^2$ would correspond to an equivalent oxide thickness $t_{eq}$ of 10 Å. Equivalent oxide thickness represents the theoretical thickness of $SiO_2$ that would be required to achieve the same capacitance density as the dielectric ignoring issues such as leakage current and reliability. $HfO_2$ with a bulk relative permittivity of 25, therefore affords a physical thickness of 63 Å to obtain $t_{eq}$ of 10 Å. Deducing the effect of an oxide on the electronic mobility and other parameters within the silicon underneath it using all-optical methods involving either linear and/or differential spectroscopic measurements would be beneficial because it would promote in-situ and non-contact measurement of the pertinent characteristics and because it would facilitate online quality monitoring of fabricated microelectronic components.

Terahertz spectroscopy has been used to assess electronic properties of materials. Optical pump—THz probe time-resolved techniques has been used to study the dynamics of mobile charge carriers in materials before they are trapped at defect sites. In such techniques, it is well understood that both the optical pump and the THz probe are pulsed. The optical pump pulse causes photo-excitation of the carriers, while the THz probe pulse measures the carrier dynamics.

These techniques have been reportedly used on a wide variety of sample materials from semiconductors to superconductors and the like to study carrier dynamics. But none of these techniques has been able to provide an accurate estimate of defects in materials as set forth below.

SUMMARY OF THE INVENTION

The present inventors have found, surprisingly, that very thin buried layers in wafers can be analyzed using pump probe spectroscopy as described herein. The present methods provide the ability to measure atomic level interfacial defects between an oxide and single crystal substrate such as Si. In accordance with at least one embodiment, properties of buried layers such as mobility in a substrate below a dielectric layer, such as in $HfO_2$ or $SiO_2$, can be analyzed using THz radiation.

In accordance with the present invention, methods are disclosed to infer the density of defects in high κ dielectric films in a non-contact, non-invasive and non-destructive manner. THz radiation is employed to measure the change in electrical conductivity of the films before and after illumination with visible light, where the visible light photoionizes the defects thereby changing the electrical conductivity and changing the transmission (or reflection) of THz radiation from the films. The disclosed techniques can be employed to make measurements as soon as wafers are fabricated. The technology is applicable to wafers of any size. The present techniques provide rapid analysis (for example, less than one (1) minute per wafer. Furthermore, the techniques provide the ability to measure defects in a deposition reactor during or immediately after film growth.

In accordance with at least one aspect of the present invention, terahertz spectroscopy is applied to the identification of defects in material samples by using a continuous wave pump beam to illuminate the sample while terahertz probe pulses are directed at the sample. The terahertz probe pulses received from the sample, via either transmission through the sample or reflection by the sample, are measured and compared to probe pulses received and measured from an unilluminated sample. This comparison results in an estimation of defect density of the sample.

In accordance with at least one aspect of the present invention, a method is provided for identifying a desired characteristic of an object, the method comprising the steps of: illuminating the object with continuous wave laser pump beam at a predetermined wavelength related to the desired characteristic; transmitting terahertz pulses at the object; and receiving the terahertz pulses reflected by the object, so that the desired characteristic can be determined from the received terahertz pulses, measuring amplitude and phase components of the terahertz pulses received to generate first results, comparing the first results from the measuring step with second results to identify the desired characteristic, wherein the second results include amplitude and phase components of terahertz pulses received by reflection from the object in the absence of any continuous wave laser pump beam illumination. In one embodiment the method is employed to identify at least one characteristic of a buried high K dielectric layer and the desired characteristic is selected from defect density and mobility.

This method can be applied to high-K (high permittivity) dielectric materials using CW visible light as the pump beam.

BRIEF DESCRIPTION OF THE DRAWINGS

A more complete understanding of the invention may be obtained by reading the following description of specific illustrative embodiments of the invention in conjunction with the appended drawings in which:

FIG. 6 shows plots of real and imaginary components of the dielectric function as a function of frequency under the Drude and Lorentz models with FIGS. 6A and 6B showing the real and imaginary plots, respectively, under the Drude model, and FIGS. 6C and 6D showing real and imaginary plots, respectively under the Lorentz model;

FIG. 8 is schematic representation possible placements of the sample in the apparatus of FIG. 1, with FIG. 8A showing transmission oriented normal to the sample, or at a modifiable angle; FIG. 8B showing the sample at a 45 degree angle with respect to the direction of transmission, and FIG. 8C showing the sample oriented normal to the direction of transmission;

Figure 1:
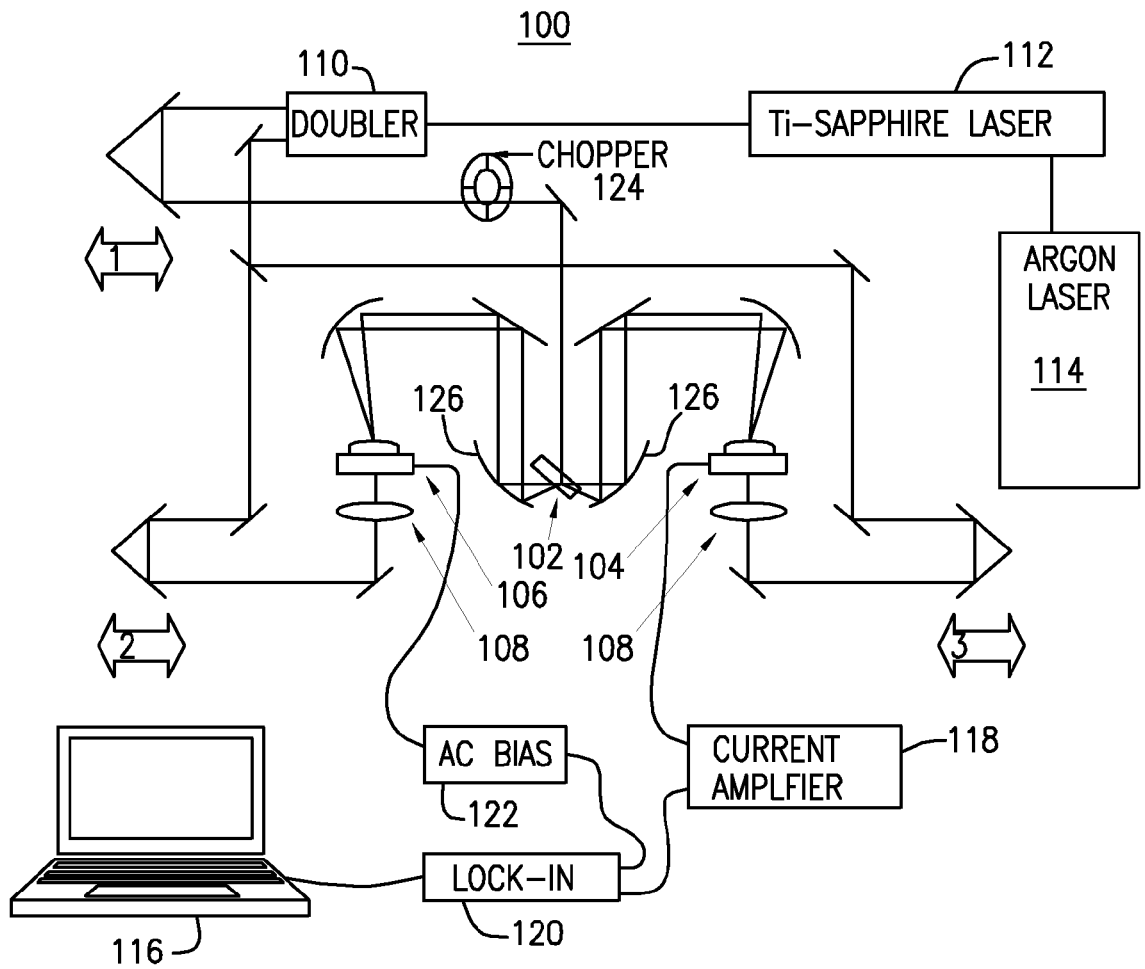
FIG. 1 shows the simplified block diagram of the continuous wave optical pump—THz probe spectroscopy system in accordance with the principles of the present invention.

It should be noted that the appended drawings illustrate only typical embodiments of this invention and are therefore not to be construed as limiting of its scope, for the invention may admit to other equally effective embodiments. Where possible, identical reference numerals have been inserted in the figures to denote identical elements.

DETAILED DESCRIPTION OF THE PREFERRED EMBODIMENTS

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

Characterization of HfO2 and SiO2 on p-type silicon, 200 mm diameter substrates using Terahertz (THz) transmission with and without optical excitation as well as reflection based THz time-domain spectroscopy is achieved in accordance with methods herein. Measurements were performed on two sets of samples, both with varying oxide thickness as well as one set having a protecting coating of either photoresist or Si3N4 deposition. The samples were identical as seen by the THz radiation for all experiments except for that under visible excitation. From these measurements the interfacial defect density due to $HfO_2$ was estimated to be 60-100 times larger than that of $SiO_2$.

FIG. 1 is a schematic of the apparatus 100 used to perform all the experiments discussed herein. Apparatus 100 can operate on sample 102 and may include transmitter 106, receiver 104, objectives 108 chopper 124, doubler 110 Ti-Sapphire laser 112, Argon laser 114, computer 116, current amplifier 118, lock-in amplifier 120, AC bias device 122. Lock-in amplifier 120 preferably uses phase-sensitive detection methods. In the above configuration, the sample 102 is placed at the focus of the THz beam (aided by off-axis parabolic reflectors 126) at a 45° angle allowing for Visible Pump/THz Probe measurements. The visible pump beam is obtained by frequency doubling 110 the pulse train from the Ti-Sapphire laser 112. It is then mechanically chopped 124. The THz pulse train is generated and detected by the aid of two similar photoconductive antennas. The modulated signal is detected through a current amplifier 118 and a lock-in amplifier 120, allowing for the waveform to be displayed on the computer 116 monitor. There are three delay lines, and depending on the experiment, one or more are translated so as to acquire the data (See Table 1).

THz-TDS

THz spectroscopy systems constructed from optical components were used to perform spectroscopic/imaging analysis on samples. One of the most common configurations, and the one on which the set-up employed in connection with the experiments discussed herein (FIG. 1) is based, is the method of THz-Time Domain Spectroscopy (THz-TDS). THz time-domain spectroscopy has been prevalent for the last twenty or so years dating back to the introduction of femtosecond duration pulsed lasers. Experiments can be characterized into transmission or reflection spectroscopy and pump-probe spectroscopy. The former, transmission spectroscopy, is probably the most widespread method used in the THz region. The advantage of this method compared to conventional methods like optical spectroscopy is that one is able to measure the time-dependent THz electric field. This means that both the amplitude and the phase of the Fourier components of the transmitted THz pulse are determined and thus the complex refractive index of the sample can be calculated, without the need for Kramers-Kronig based calculations.

The THz-TDS apparatus, which is configurable for transmission, reflection and visible pump/THz probe spectroscopy (see Table 1), is shown in FIG. 1. A femtosecond Ti-Sapphire laser (NJA-4, Clark-MXR Technologies) at an 82 MHz reprate drives the whole spectrometer. An extremely fast pulse (e.g. with a pulse duration of ~80 fs), measured with an Optical Spectrum Analyzer), p-polarized, from the laser is divided into two parts by a beam splitter. The first part (probe pulse) irradiates the transmitter, generating a THz electric transient. The second part (called gating or sampling pulse) gates the detector, i.e. the detector measures, what was the instantaneous THz field at the moment of the gating pulse arrival. In essence, THz time-domain spectroscopy is the process of measuring the shape of the whole THz pulse by delaying the gating pulse.

TABLE 1

Experimental Configurations for THz-TDS Apparatus (FIG. 1)

| Type of Experiment | Fix | Move | Reference (chop) |
|---|---|---|---|
| Reflection/Transmission | 1 (off) | 2 or 3 | 2 |
| Visible Pump/THz Probe[1] | 1 and 3 | 2 for diff. fixed pos. of 1 | 2 or 1 |
| Visible Pump/THz Probe[2] | 1 and 3 | 2 | 1 |
| THz Emission Spectroscopy | 2 and 3 | 1 | 1 |

[1]Time-resolved pump transmission to probe recombination lifetime
[2]For peak carrier density corresponding to peak average optical excitation intensity, to generate THz waveform due to excited carriers.

THz Generation

Figure 2:
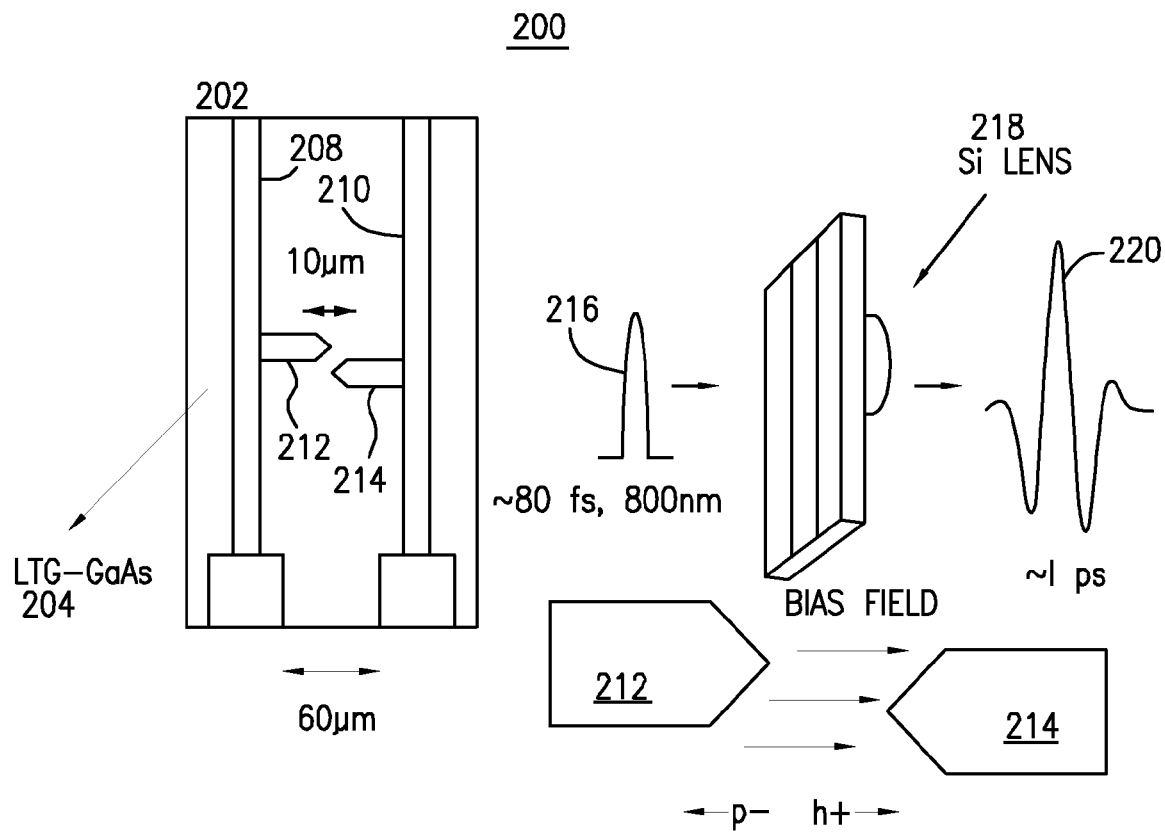
FIG. 2 is block diagram of an antenna suitable for use with an embodiment of the present invention.

The photoconducting antenna is based on a design pioneered by D. H. Auston (1984) and refined by Yi Cai (1997) and Oleg Mitrofanov (2001). Antennas used in experiments were manufactured with Oleg Mitrofanov at Bell Labs-Lucent Technologies, Murray Hill, N.J. The antenna is basically a metal transmission line structure deposited on LTG-GaAs substrate (FIG. 2). LTG-GaAs is obtained by growing epitaxial layers of GaAs using Molecular Beam Epitaxy (MBE) and is annealed at low temperatures (~600° C.). With reference to FIG. 2, after the sub-100 fs visible (λ~800 nm) pulse is focused on the gap (~10 μm) of the dipole structure 212, 214 under a DC or AC bias, a THz pulse/transient 216 is emitted and defocused onto a off-axis parabolic reflector with the aid of a silicon hemisperical lens 218 on the backside of the antenna 202 substrate. The antenna 202 can include transmission lines 208, 210 (which may be made of Gold) deposited on a LTG-GaAs substrate.

The transmission lines 208, 210 each are 10 microns wide and are separated by 60-100 microns. There is a dipole structure 212, 214 with a gap of 5-10 microns to which the visible pulse is focused on to at a spot size of about 10 microns.

Figure 3A:
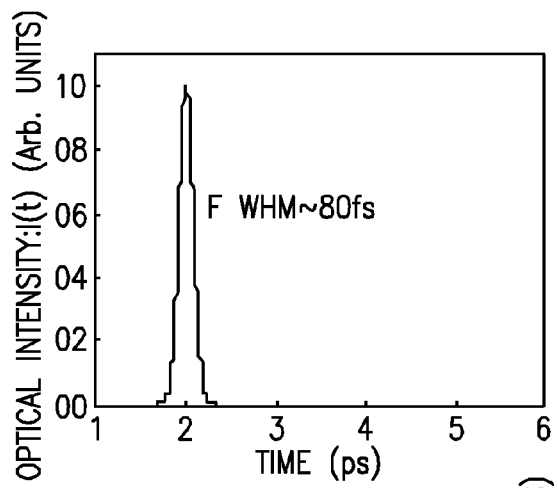
FIG. 3A is a graph of the optical intensity versus time for the antenna of FIG. 2.
Figure 3B:
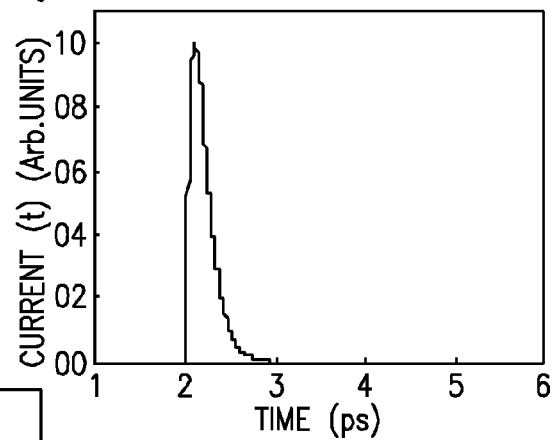
FIG. 3B is graph of the current generated as a function of time by the antenna of FIG. 2.
Figure 3C:
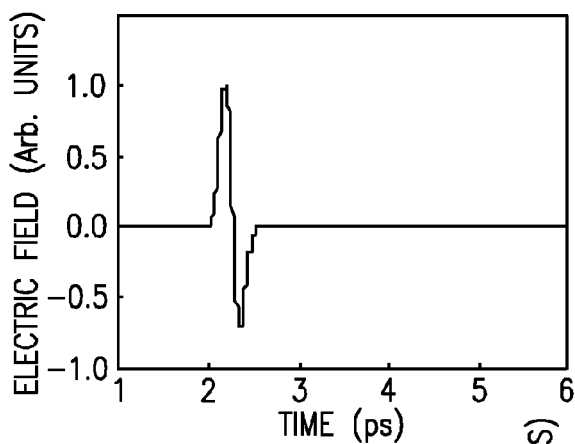
FIG. 3C is a graph of the electric field versus time for the antenna of FIG. 2.
Figure 3D:
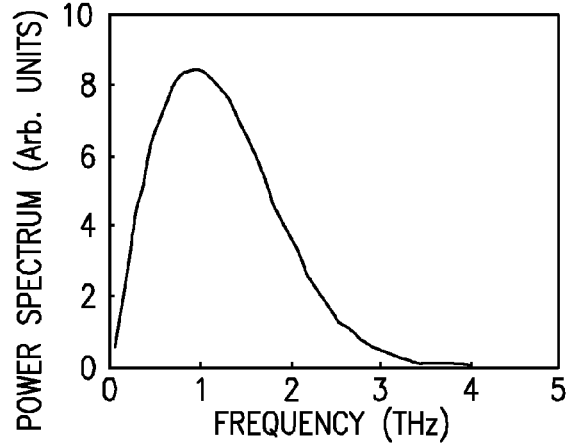
FIG. 3D is a graph of power versus time for the antenna of FIG. 2.

An alternating (AC) or constant (DC) bias is applied to the transmission line structure in order to accelerate created electron-hole pairs. It is important to note however that a surface depletion field can also act as the bias for the carrier acceleration. See, Zhang, X. C., Hu, B. B., Darrow, J. T., and Auston, D. H., "Generation of femtosecond electromagnetic pulses from semiconductor surfaces," Appl. Phys. Lett., 56 (11), 1011-1013 (1990). In this case, the electric field is perpendicular to the surface of the transmitter contrary to the former where it is parallel. After the visible pulse with energy above the semiconductor bandgap arrives, carriers are excited in to the conduction bands. These free-carriers or electron-hole pairs are generated at a rate that is proportional to the intensity profile of the incident pulse. The generation rate corresponding to the electron-hole pairs rises rapidly also in part due to the external bias. The dynamics of the emitter/photoconductive antenna under bias resulting in the generation of the THz transient are shown in FIG. 3. FIG. 3A is a plot of optical intensity occurring as the 80 fs visible pulse leads to a fast response. FIG. 3B shows generated current which decays with recombination lifetime. The fast rise of the current leads to the generation of a THz transient as shown in FIG. 3C. When detected as outlined in the discussion, the time-domain waveform can be transformed using FFT methods to obtain the frequency domain spectrum. The power spectrum is shown in FIG. 3D.

The fast rise of the transient current results in a THz pulse (few picoseconds in duration) being radiated into free space. The photogenerated carriers then recombine, and the current in the dipole returns to its initial value. This whole process repeats with the arrival of the next optical pulse. The pattern of the radiation emitted into free space is complicated due to the thickness of the substrate as well as the silicon lens on the backside used to collimate the THz radiation. The dipole structure of the antenna predicts that the far-field on-axis radiation would follow the expression:

$$E(t) = \frac{1}{4\pi\varepsilon_o rc^2} \frac{\partial^2 p(t)}{\partial t^2} \quad (2.1)$$

Where, p(t) is the dipole moment, c the speed of light, $\varepsilon_o$, permittivity of free space, and r is the distance from the dipole. Assuming the length of the dipole to be a, $$I(t) = a\frac{\partial p(t)}{\partial t} \quad (2.2)$$

then, $$E(t) \propto \frac{\partial I(t)}{\partial t} \quad (2.3)$$

In addition, the radiated field also depends on the photo-excited static charge density. A detailed explanation of the characteristics of the radiated field and its transient current dependency can be found in Mitrofanov, O., "Near-Field Imaging with THz pulses," Dissertation, NJIT, Newark, N.J. (2001), incorporated herein by reference. It has been pointed out that the THz Electric field strength radiated away can increase if the visible pulse is focused close to the electrode end. This type of variability in THz electric field strength due to the position and shape of the focus of the visible pulse has prompted many to fabricate THz-fiber coupled emitters, where the position of the visible beam is always the same on the dipole. Cai, Y., "Enhanced terahertz pulse generation and detection using electric-field singularities in photo-conducting antennas," Dissertation, NJIT, Newark, N.J. (1998), incorporated in full herein by reference. In the present apparatus, the average generated THz power is estimated to be on the order of a few microwatts with a horizontal to vertical polarization ratio of 4:1. Cai, Y., "Enhanced terahertz pulse generation and detection using electric-field singularities in photo-conducting antennas," Dissertation, NJIT, Newark, N.J. (1998).

THz Detection

Figure 4:
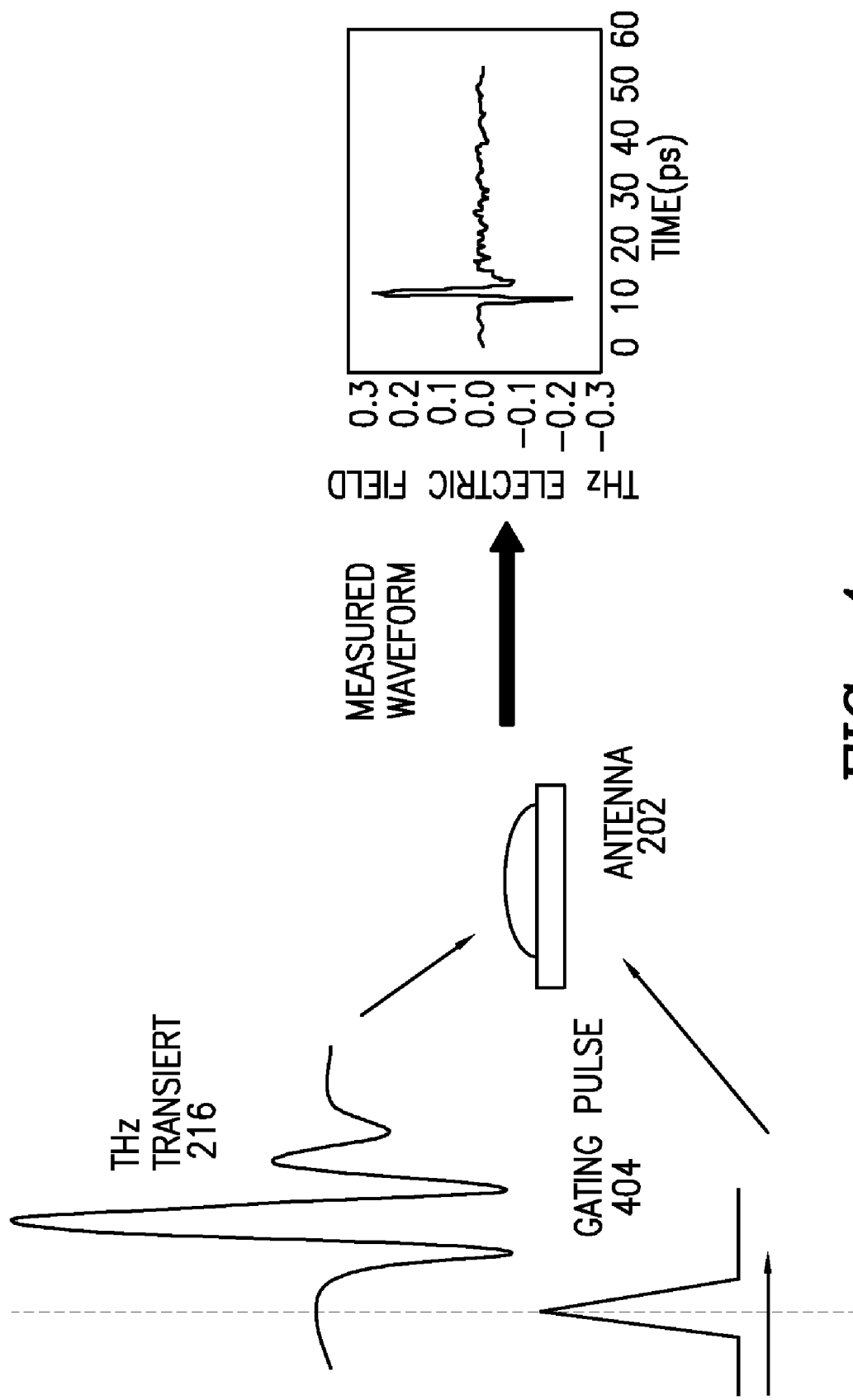
FIG. 4 is a block diagram showing signal transmission to an antenna and a graph of the signal measured thereat in accordance with an embodiment of the present invention.

The eloquence of the THz-TDS method is even better realized with the fact that the transmitter structure duplicates as a receiver/detector. Here the relative arrival of the THz transient and the gating optical pulse are varied in time so that the entire THz waveform can be mapped out (FIG. 4). This detection method allows one to measure both the amplitude and phase of the THz field unlike square-law (Signal∝$E^2$∝I) detectors that measure intensity only. Nonetheless, due to the response function of the detector, the measured THz waveform is not exactly the same as the generated one, and depending on the experiment one skilled in the art would recognize this should be taken into consideration.

With reference to FIG. 4, the THz transient 216 is detected through the backside of a structure identical or almost identical to the emitter structure photoconductive antenna 202 with the aid of an off-axis parabolic mirror. The beam is focused on to the hemisperical silicon lens which focuses again to the dipole antenna 202. The gating pulse 404 (arriving in same phase at the dipole with the THz pulse 216 since it is split from the same visible pulse train used to generate the THz through the emitter) probes the THz waveform amplitude. Any point on the THz waveform acts like the bias in the emitter structure allowing for the charge to flow across the dipole gap at a magnitude that is proportional to the amplitude of the THz transient 216 at that point. By delaying the time separation between the visible gating pulse 404 and the THz pulse 216, one can map out the entire THz waveform in the time-domain. The foregoing is the preferred way of using THz-TDS. Note: electro-optical detection could have been used in place of the above-described method (which would entail using a ZnTe crystal instead of photoconducting antenna).

Figure 5A:
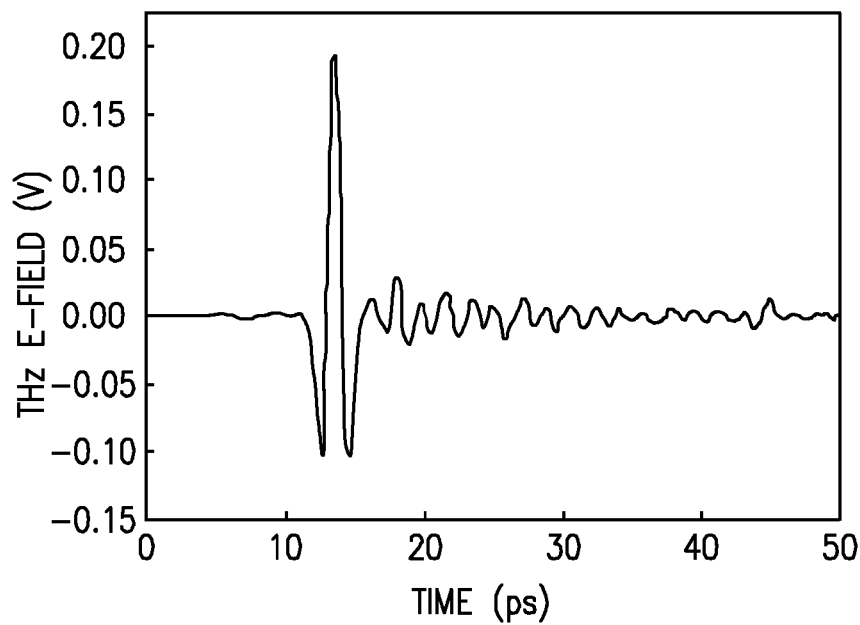
FIG. 5A is graph of the electric field of air as a function of time.
Figure 5B:
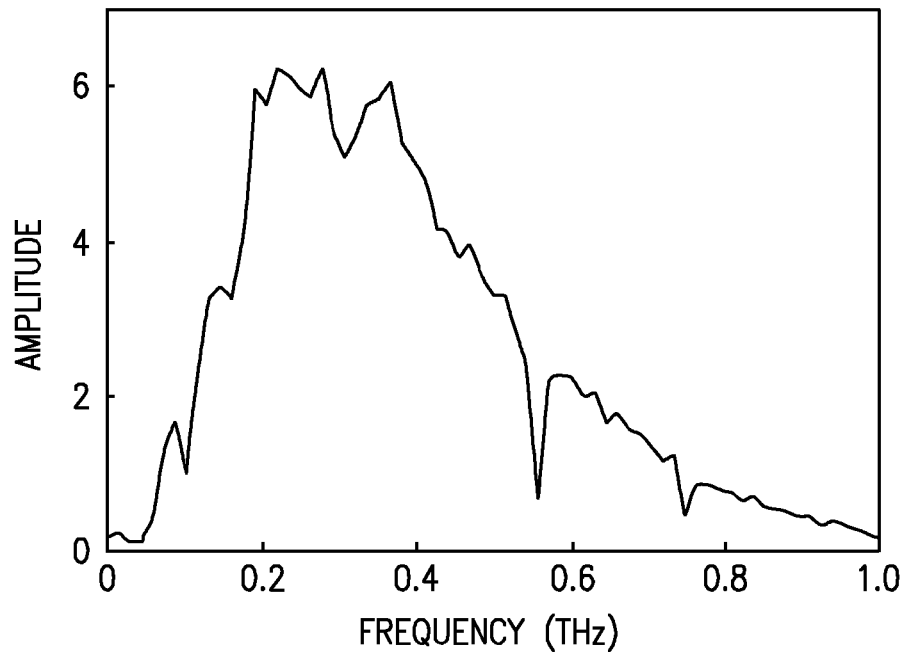
FIG. 5B is graph of a Fast Fourier Transform of the graph of FIG. 5A showing amplitude plotted against frequency.

The detection method is based on a similar mechanism to the transmitter. Since the carrier recombination rate (200-300 fs is much shorter than the THz transient is (~few ps), the detector works like a sampling gate. The antenna is activated by the arrival of the optical pulse focused onto the gap, which generates electron-hole pairs and the resistance of the medium drops. The THz-transient electric field is focused onto the same gap, and acts as a bias, allowing current to flow through the dipole. The total amount of the transported charge is proportional to the instantaneous THz electric field. Since the visible pulses used to generate and detect the THz field come from the same source, they arrive at the detector with the same phase so that one can delay one pulse with respect to another to map out the entire THz waveform (FIG. 5). FIG. 5 shows THz-TDS of Air. FIG. 5A shows a time-domain scan; and FIG. 5B shows the FFT (Fast Fourier Transform) of the plot of FIG. 5A, showing main water absorption features at frequencies of 0.57 THz and 0.78 THz. Note that the electric field is measured in volts through our detection scheme (lock-in), and even though the spectrum is terminated at 1 THz, the signal amplitude decreases at frequencies above 0.75 THz.

The bandwidth of the detector is determined by two factors: The photoconductive response to optical excitation and the frequency dependent response of the antenna structure. The detector response imposes the high frequency limit, due to the finite duration of the sampling intervals (carrier lifetime in LTG-GaAs).

The second factor that limits the bandwidth is the resonance properties of the dipole antenna, due to the length of the dipole. Its length determines a resonance frequency to which the spectrum peaks, thus the central frequency of the obtained spectrum can be tuned by varying the length of the dipole.

This is eliminated when the sample spectrum is normalized to a reference spectrum (discussed in next section) measured with similar receiver/transmitter pair of antennas. The transmitter used was 60 μm-10 μm (distance between transmission lines-gap width), and the receiver was 60 μm-5 μm. Employing the pair discussed, an upper limit for the bandwidth to about 1 THz was achieved.

Parabolic mirrors are used to collimate and transmit the generated THz pulse through a path length of approximately 0.85 m (FIG. 1). In most instances, an enclosure was placed around this region and air inside was purged with dry nitrogen. This effectively reduces the absorption by water (FIG. 5). Once the THz pulse is received at the detector, the current (few picoamps) is detected through a current amplifier (Ithaco Model 1211), and the waveform is plotted through a lock-in amplifier phased with respect to modulation of the THz transient. This modulation can be achieved either by mechanically chopping the visible beam focused onto the transmitter or by applying an AC bias with a digital function generator (HP 38120A) on the transmitter. The THz waveform is then mapped out by varying a mechanical delay line and recorded though software routines written in LabView™ on a personal computer.

THz Spectral Analysis

Optical properties of the medium are directly obtained from the time domain measurements. The time-dependent THz electric field is given by:

$$E(t) = \frac{1}{\sqrt{2\pi}} \int_{-\infty}^{\infty} E(\omega) \cdot e^{-i\omega t} d\omega \quad (2.4)$$

thus, in the frequency domain $$E(\omega) = \frac{1}{\sqrt{2\pi}} \int_{-\infty}^{\infty} E(t) \cdot e^{-i\omega t} dt \quad (2.5)$$

this is complex and can be expressed as, $$E(\omega) = A(\omega) e^{i\phi(\omega)} \quad (2.6)$$

where, $A(\omega)$ is the magnitude. The above equation states that the spectrum obtained by utilizing the THz-TDS technique has the advantage of providing phase information of the propagating pulse. Most materials are dispersive, i.e. the dielectric constant is a function of frequency $\in(\omega) = \tilde{n}^2(\omega)$ THz-TDS allows the imaginary and real parts of the index of refraction of the sample in question to be extracted since changes in the THz waveform describe absorption and dispersion from the media. If the complex index of the media under examination is given by:

$$\tilde{n} = n + ik \quad (2.7)$$

then, the THz E-field is modified after traveling a distance (d) through the dispersive medium to:

$$E(t, d) = \frac{1}{\sqrt{2\pi}} \int_{-\infty}^{\infty} E(\omega) \cdot e^{i\frac{\omega n d}{c}} e^{-\frac{\omega k d}{c}} e^{-i\omega t} d\omega \quad (2.8)$$

Absorption changes the shape of the waveform by incorporating "ringing"-long lasting electric field oscillations, which follow the main transient pulse as well as reduction in the measured amplitude. These changes can be quantified by analyzing the time-domain scans in the frequency domain and referencing them to a scan (spectral analysis requires a Fast-Fourier Transform (FFT) applied to the time domain data) where the sample is not present. Noise and spectral measurement parameters limit the sensitivity of these measurements.

Sensitivity and Measurement Uncertainty

Noise can be characterized as a background/white noise-due to the detector and instruments and a systematic noise due to the optical pulses gating the transmitter and receiver. While the LTG-GaAs antennas have very high power sensitivity per square root frequency, the carrier lifetime due to the gating pulse that defines the maximum detectable frequency of the THz transient limits the signal measurements. The stability of optical pulses generated through the Ti:Sapphire laser, i.e. amplitude, spectral variations over time, depends on a large part on the stability of the argon laser. These effects become important when performing measurements that require long time intervals between each time step of the mechanical delay line (a delay of roughly the 1/e value-3 times the measurement time window-of the lock-in to ensure that it will precisely measure the signal as the delay line is stepped). However, most of the noise is probably due to the instruments. Specialized current amplifiers that are constructed right near the antenna structure and that can detect down to femtoampere levels can be used to increase sensitivity, but can reduce signal strength without appreciable (if any) change in the signal to noise. Employing the apparatus as described, signal to noise measurements on the order of 500:1 were achieved.

The length of the waveform determines the spectral resolution of the instrument. To obtain high-resolution spectra a long time-domain scan is required. Contrary, a narrow time window allows for the detection of broad spectral peaks and can also be used to eliminate the Fabry-Perot type interference effects that can be incurred from multiple reflections as the pulse propagates through the sample. These interference effects can also be removed numerically in the post-spectral analysis of the THz pulse. While the upper limit of the THz-TDS technique is limited by detector bandwidth, the lower limit is given by the spectral resolution.

THz-TDS upon Reflection/Transmission

The described apparatus permits measurements to be performed for several configurations: Transmission, Reflection, Emission, and Visible-Pump/THz Probe Spectroscopy (FIG. 8). FIG. 8 shows three configurations available using the apparatus of FIG. 1. FIG. 8A shows THz-TDS transmission in a direction normal to the interface or at an angle. FIG. 8B shows a configuration in which visible-Pump/THz Probe measurements may be made with the transmission direction oriented at a 45 degree orientation with respect to the sample, thereby assuring that the arrival of the pump pulse (~1 cm spot size) coincides with the arrival of the THz pulse (~3 mm spot size) on the backside of the sample 102. FIG. 8C shows yet another configuration of the apparatus of FIG. 1.

The real advantage of a time resolved-spectroscopic method like THz-TDS compared with other frequency based methods (such as FTIR) is the ability to deduce material properties directly from the time-domain data. For example, the real index of a material can be deduced directly from the time-domain scan by examining the relative phase delay between incident and transmitted pulse (FIG. 1) once the thickness is known. Another advantage of a time-resolved measurement technique is to examine carrier dynamics in photoexcited semiconducting samples. If the impinging light has sufficient energy to excite carriers from the valence to the conduction band, then the transmitted or reflected THz electric field will be absorbed proportionally to the carriers that have not yet recombined in the characteristic recombination time ($\tau_r$). This technique is discussed extensively as applied to LTG-GaAs and other materials whose response time is faster than the duration of the THz transient.

In Transmission and Reflection spectroscopy, scans are normalized (transmitted or reflected field normalized to incident field) to extract frequency dependent parameters of a medium with thickness d (which are obtained from equation 2.8):

$$n = \frac{c}{\omega d}[\varphi(\omega, d) - \varphi(\omega)] \qquad (2.9)$$

And, $$k = \frac{c}{\omega d} \ln\left(\frac{A(\omega, d)}{A(\omega)}\right) \qquad (2.10)$$

One can also easily obtain the absorption coefficient of any sample if the thickness is known:

$$\alpha = \frac{2k\omega}{c} \qquad (2.11)$$

Or, $$\alpha = \frac{1}{d}\ln\left(\frac{I}{I_o}\right) \qquad (2.12)$$

Where I is the intensity after passing and $I_o$ is the initial intensity on the sample. Once any of the above parameters have been obtained experimentally, others such as conductivity, mobility, etc. can be extracted from an appropriate conduction model.

Metals, semi-metals and insulators each have different electronic characteristics. In the THz region most metals are opaque while insulating materials are purely transmitting. For example, in the far-IR, reflectance from a metal can be explained by the Drude model or free-carrier dispersion model (see, Hummel, R. E., "Electronic Properties of Materials," 2nd Ed, Springer-Verlag (2003)):

$$\varepsilon(\omega) = \varepsilon_\infty - \frac{\omega_p^2}{\omega(\omega + i/\tau)} \qquad (2.13)$$

where, $\varepsilon_\infty$ is the dielectric constant of the material at high frequencies, $1/\tau$ is the collision frequency, $\omega_p = (4\pi N e^2/m)^{1/2}$, N, e, m are the plasma frequency, number density, charge and mass of the free carriers, respectively. While in the visible wavelengths its spectrum can be well fit with Lorentz model or local oscillator/bound charges model:

$$\varepsilon(\omega) = \varepsilon_\infty - \sum_{m=1}^{M} \frac{\Omega_m^2}{(\omega^2 - \omega_m^2) + i\Gamma_m\omega} \qquad (2.14)$$

Where, $\Omega_m$, $\omega_m$, $\Gamma_m$, and M are the oscillator strength, resonant frequency, resonant width, and number of resonances, respectively. From the band structure of various materials we can characterize metals which have overlapping bands to follow Drude, and insulators that have wide gaps between bands to follow Lorentz like conductivity models. Semi-metals or semiconductors, can display characteristics which can be described by either Drude, Lorentz or a combination of both depending on the band structure and the region of the electromagnetic spectrum the sample is characterized in:

$$\varepsilon(\omega) = \varepsilon_\infty - \frac{\omega_p^2}{\omega(\omega + i/\tau)} - \sum_{m=1}^{M} \frac{\Omega_m^2}{(\omega^2 - \omega_m^2) + i\Gamma_m\omega} \qquad (2.15)$$

In addition to above conduction mechanisms due to interband and intraband absorption, vibrational excitations (phonons) that manifest as very narrow localized absorption features can also modify the response of a material as seen in transmission/reflection spectra. These phonons are also modeled by harmonic oscillators.

In the particular case of bulk semiconductors with low impurities or defects, due to the low energy (THz) spectral range of the THz-TDS system, the reflection and transmission measurements will follow a pure Drude model, so that only intraband transition energies of carriers in the valence or conduction bands are explored. However, in certain cases there is evidence for localized states that can be modeled with a Lorentz model. In both, interactions with phonons can be ruled out, since the spectral range from 0.1 to 1 THz is below the typical energies of acoustic and optical phonons which usually have very narrow line widths. In addition, at room temperature (~26 meV) phonon assisted transitions with energy below this set-point are not only highly unlikely but have broadened as well so as to not contribute much in the transmission/reflection spectra.

Upon examining the models discussed so far, two approaches can be taken towards analyzing the electronic parameters of any type of sample in the THz region. By extracting the real and imaginary index from the phase shift and absorption coefficient respectively, one can determine the plasma frequency and conductivity/mobility of the sample under examination (this approach assumes that the sample is thick enough so phase information can be obtained). The other approach is to extract a carrier density (corresponding plasma frequency) and scattering rate from the Drude model representation of the index of refraction, $n(\omega) = \sqrt{\varepsilon(\omega)}$, after the index of refraction is extracted from the transmission and or reflection coefficients. If the structure of the sample is known, then the reflection/transmission coefficient can be modeled with a Kramers-Kronig based analysis of the different media in the path of the THz transient. Furthermore, if the sample has both Drude and Lorentz-like properties, then the Lorentz parameters that govern the transmission/reflection spectra can be extracted similarly. The latter is the method of analysis undertaken in the applications discussed here since the thickness of the layers in samples analyzed were too small compared to the THz wavelength so that the real and imaginary index could not be extracted directly from the measurements.

In the Transmission configuration, the THz beam was focused to a 3 mm spot size onto the sample surface with the aid of a parabolic mirror. The sample can be rotated in the p- and s-planes allowing for polarization dependent measurements.

When the sample is non-transmittive and impedes one from accurately measuring its electrical characteristics, reflection based measurements can be employed depending on the sample size with respect to the diameter of the THz beam.

In the reflection configuration, the sample is preferably placed near one of the flat gold mirrors, with a THz beam spot size of roughly 40 mm. Reference scans in this case are from the surface of the gold mirror, i.e. a perfect reflector in the far-IR. In both cases, the presence of water absorption lines needs to be acknowledged since they will affect the spectrum (FIG. 2.6).

THz Emission Spectroscopy

The Emission spectroscopy method for characterizing a sample is performed with samples for which the pumping pulse can generate a THz transient. The shape of the THz waveform emitted from the sample after the irradiation by ultra short optical pulse holds information about transient current density or polarization. If the response of the sample and the detector can be estimated then the theoretical expected THz waveform can be constructed and compared with measured values to estimate electrical parameters. See, Nemec, H., "Application of methods in time-domain terahertz spectroscopy for investigation of ultra fast dynamics in condensed matters," Diploma Thesis, Charles University in Prague, Czech Republic (2002). This technique was used for example to investigate quantum structures (Planken, P. C. M., Nuss, M. C., Brener, I., and Goossen, K. W., "Terahertz emission in single quantum wells after coherent excitation of light hole and heavy hole excitons," Phys. Rev. Lett., 69 (26), 3800-3803 (1992)); semiconductor surfaces (Zhang, X. C., and Auston, D. H., "Optoelectronic measurement of semiconductor surfaces and interfaces with femtosecond optics," J. Appl. Phys., 71 (1), 326-338 (1992)); cold plasma (Kersting, R., Unterrainer, K., Strasser, G., Kaufmann, H. F., and Gornik, E., "Few cycle THz emission from cold plasma oscillations," Phys. Rev. Lett., 79 (16), 3038-3041 (1997)) and influence of magnetic field on carrier dynamics (McLaughlin, R., Corchia, A., Johnston, M. B., Chen, Q., Ciesla, C. M., Amone, D. D., Jones, G. A. C., Linfield, E. H., Davies, A. G., and Pepper, M., "Enhanced coherent terahertz emission from indium arsenide in the presence of a magnetic field," Appl. Phys. Lett., 76 (15), 2038-2040 (2000)).

Visible Pump/THz Probe Spectroscopy

Pump-probe spectroscopy is very suitable for investigations of ultrafast dynamics. Visible pump/THz probe spectroscopy is similar to techniques employed in visible to near-IR regimes. Both amplitude and phase changes in the probe (THz) induced by effects from the sample due to the pump can be measured. Here, the probing pulse directly probes the response of the induced carriers or phonons. In an optical pump-THz probe experiment the changes in the response of the sample induced by the arrival of ultrafast optical pulse are studied by probing the sample with a delayed THz pulse (FIG. 8*b*). The excitation and THz beams are synchronized since they derive from the same ultrafast laser pulse. The principal interaction in most instances is the absorption of the THz pulse by free carriers. Pump measurements can either be performed at 400 nm (by frequency doubling the 800 nm light though a lithium triborate (LBO) crystal), or 800 nm, with pump-pulse peak energies on the order of a few nanojoules.

Figure 9B:
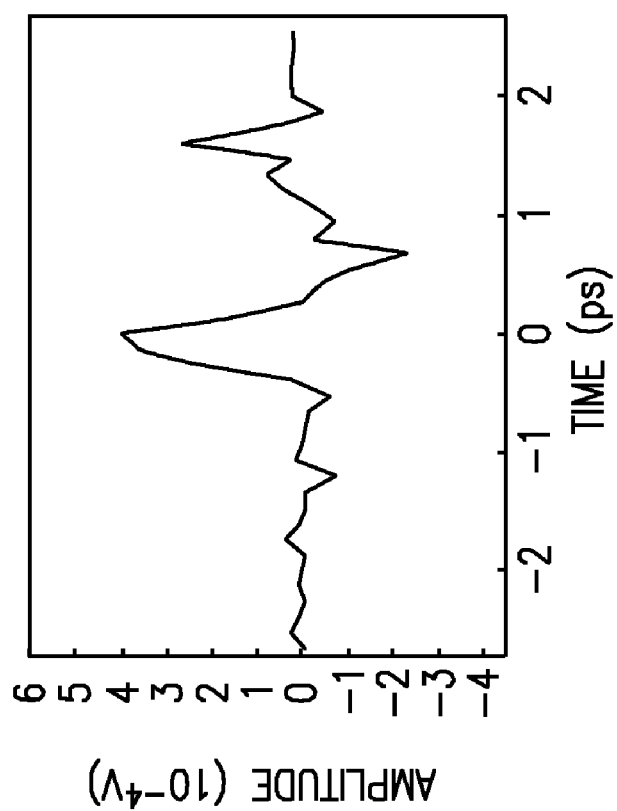
FIG. 9B is graph of carrier lifetime decay against time according to another embodiment of the invention.

Visible pump (λ-400 nm)-THz probe experiments on [100] oriented LTG-GaAs grown on a GaAs substrate were conducted. The carrier dynamics after the arrival of the visible photoexcitation is very similar to the THz transient generation dynamics discussed earlier. Because the visible excitation is at 400 nm, its penetration depth is limited to within 1 micron in the LTG-GaAs layer. See, Beard, M. C., Turner, G. M., and Schmuttenmaer, C. A., "Sub-picosecond carrier dynamics in low-temperature grown GaAs as measured by time-resolved THz spectroscopy." J. Appl. Phys., 90, 5915-5923 (2001). Either THz-Emission spectroscopy or time resolved THz-TDS technique can be done to probe the carrier lifetime. In the first case, since the visible pulse will generate a THz transient it is possible to deduce the recombination lifetime of the carriers by analyzing the generated waveform. In the latter case, the pumping pulse can be adjusted so as to arrive just before the THz pulse enabling the carrier-lifetime to be probed. When utilizing this method, specifically any THz-TDS based technique, the situation is a little more complicated since the carrier dynamics can be on scales that are faster than the duration of the probing pulse (few ps). When the THz probing pulse arrives, it is expected the amplitude of the generated THz transient from the sample to decrease. This occurs, since free carriers which not yet have recombined absorb the THz probe. However, in the instance that the duration of the THz pulse (few ps) is comparable to the recombination lifetime (~1 ps) the experiment should be performed so as to not skew the results. This places limitations on which delay lines are scanned as shown in FIG. 1. If the generated carriers respond in a time duration greater than the THz pulse then the lifetime can be probed with 1-line configuration scan (pump or probe). See, Beard, M. C., and Schmuttenmaer, C. A., "Using the Finite-Difference Time-Domain Pulse Propagation Method to Simulate Time-Resolved THz Experiments" J. Chem. Phys., 114, 2903 (2001). For times less than the duration of the THz pulse, the THz transient will not only be absorbed by photogenerated carriers but also will experience any changes in the index of refraction due to pumping so that any absorption will have frequency dependence. Because of this effect, visible pump/THz probe (1-line scanning implying moving delay lines 1 (pump) or 3 (receiver), see FIG. 1, while keeping 2 (transmitter) fixed) can not be used to deduce lifetimes of materials whose response is short or comparable to the THz pulse duration. This was the case for one particular experiment conducted on LTG-GaAs. FIG. 9*b* shows the change in THz transmission ΔE (since the sample itself generates a transient, so one skilled in the art must take the difference scan between pump on and pump off) taken by keeping delay line 2 fixed and scanning delay line 1. These results, as shown, cannot be analyzed to extract recombination lifetime.

To analyze the recombination lifetime of such materials (whose response is faster than the duration of the THz pulse or recombination lifetime comparable or less than the duration of the THz pulse) one can employ Time Resolved THz Spectroscopy (TRTS) measurement technique. In TRTS, any changes in the THz pulse are analyzed with respect to the probe delay and the pump delay. See, Beard, M. C., Turner, G. M., and Schmuttenmaer, C. A., "Sub-picosecond carrier dynamics in low-temperature grown GaAs as measured by time-resolved THz spectroscopy." J. Appl. Phys., 90, 5915-5923 (2001) It is inherently non-linear because of these two temporal variables: the arrival of the pump pulse relative to the arrival of the THz pulse, and the propagation time of the THz pulse. The arrival of the visible pulse introduces a transient polarization in the sample, which will affect the propagation of the THz pulse. This is why TRTS is sometimes referred to as a 2-line scan. By moving the transmitter (2) for fixed pump (1) -probe (2) time delays one can map out the change in THz transmission. Equally, both delay lines 1 and 3 can be scanned together while keeping delay line 2 fixed. Either scenario results in every portion of the measured THz transient experiencing the same delay from the visible pulse. Then the photogenerated carrier lifetime can be extracted as long as one deconvolutes the effects with an exponential function representing the recombination of carriers and a Gaussian function representing the excitation pulse width.

In addition to the dynamical dependence of the pump-probe delay the other limitation is at the detector. Detector response (~300 fs) limits the time-resolved resolution of THz absorption, so that effectively places a lower limit on the types of materials that can be studied. The response of the detector should to be taken into consideration and deconvoluted from the overall model to extract carrier lifetimes for "fast decay" samples. See, Beard, M. C., Turner, G. M., and Schmuttenmaer, C. A., "Sub-picosecond carrier dynamics in low-temperature grown GaAs as measured by time-resolved THz spectroscopy." J. Appl. Phys., 90, 5915-5923 (2001).

Figure 9A:
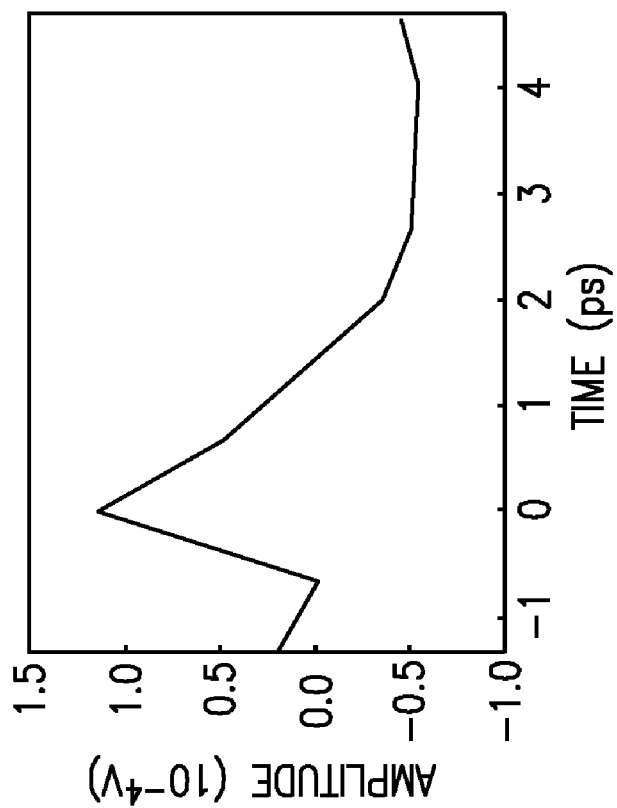
FIG. 9A is a graph of carrier lifetime decay against time according to one embodiment of the invention.

FIG. 9 shows visible pump/THz Probe measurement showing carrier lifetime decay of LTG-GaAs. The pump was centered on 400 nm, with $P_{av}$~3 mW/cm$^2$. The plot of FIG. 9A arises from a scan which was taken by moving delay line 2 and keeping delay line 1 fixed for different positions (2-line scan). The plot of FIG. 9B was acquired by moving delay line 1 and keeping delay line 2 fixed (a 1-line scan; see FIG. 1). Since the sample itself generates a THz transient when illuminated with a visible pump pulse, a difference ($\Delta E$) scan of the THz transmission through LTG-GaAs is shown in FIG. 9a. By only considering the response to follow an exponential decay we extract the carrier lifetime to be $\tau$=2.43 ps. This is much larger than what we expect (<1 ps). The long decay suggests that there are other effects from the sample that need to be considered when extracting recombination lifetimes on such short scales.

Differential spectroscopy, which is a variant of Visible Pump/THz probe spectroscopy, is where the THz probe analyzes not the short lived carriers, but the carrier generation envelope at a fixed point. In these experiments the probe pulse is scanned while the pump is fixed. This way, one can obtain the effect of the peak-carrier generation on the THz transmission. This configuration of visible pumping allows demonstration of a time-averaged optically induced change in the transport properties of a layer.

Experiments

Samples Studied

Figure 10:
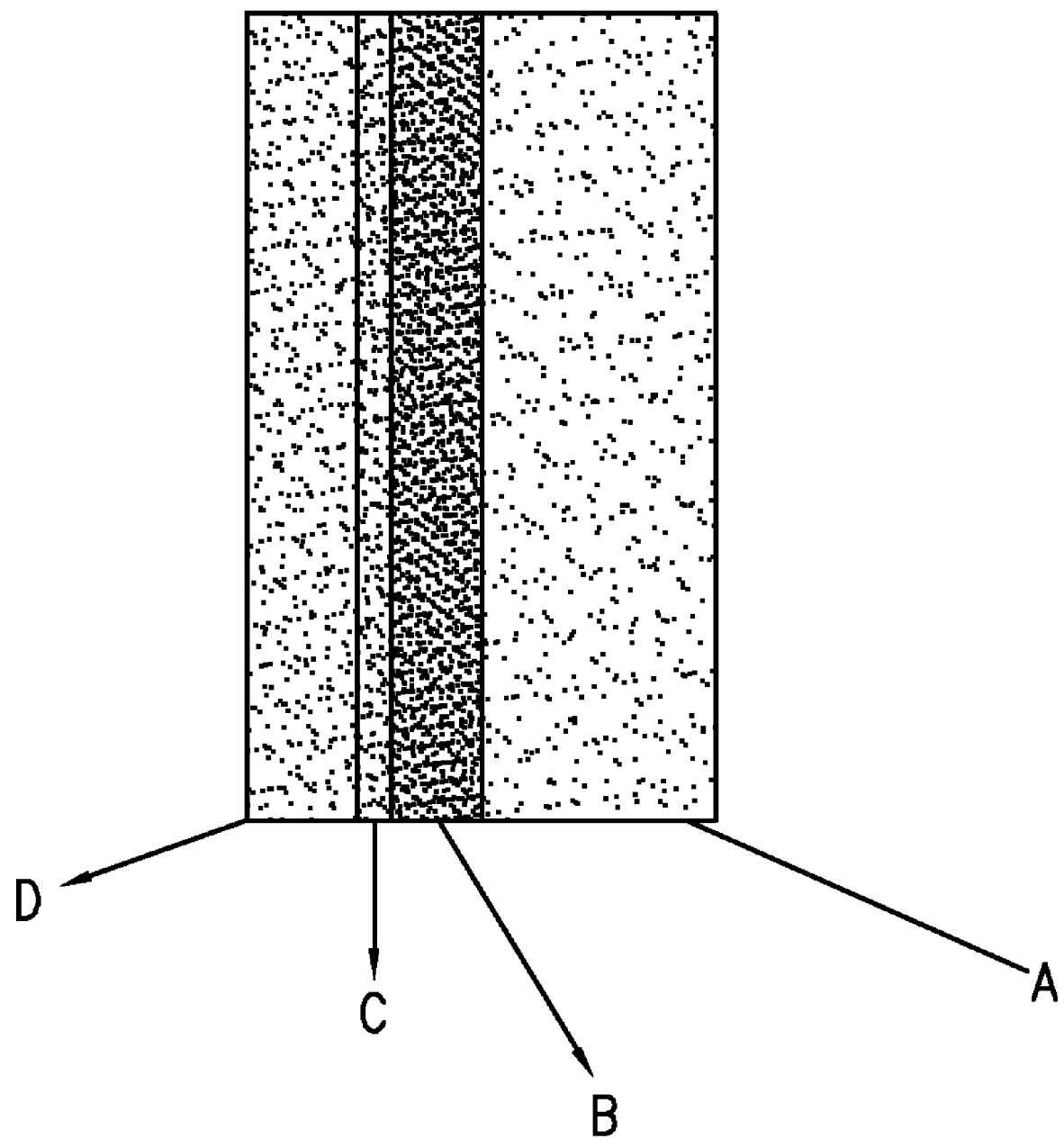
FIG. 10 is sectional view of a wafer in accordance with an embodiment of the invention.

Wafers subjected to analysis were provided by Sematech Inc. FIG. 10 shows a wafer including silicon substrate A, P+ silicon layer B, oxide layer C (which may be hafnium dioxide or silicon dioxide), and coating D, which may be photoresist or $Si_3N_4$. Sample wafers were 20 cm in diameter and were protected by either a 3000 angstrom thick coating of photoresist (PR) or by an amorphous 200 angstrom thick nitride deposition (ND or $Si_3N_4$) on top of the dielectric materials. The thickness of the HfO2 was either 70 or 100 Å, and the thickness of the SiO$_2$ was 50 Å. These samples were deposited on a heavily doped p+ layer (Boron doping~$10^{18}$ cm$^{-3}$, 300 Å thick) which separated the dielectric from the p-type silicon substrate. Finally there was the p-type Silicon substrate of thickness 500 μm. In addition, different control samples, each coated with either photoresist or $Si_3N_4$ without any oxide layer was provided.

Reflection THz-TDS, Transmission THz-TDS and Visible Pump/THz Probe experiments were performed to determine the optoelectronic characteristics of HfO2 and SiO2 coated wafers. The first batch of dielectric coated wafers did not readily transmit the THz pulse, possibly due to polishing treatments done on the backside of the wafers. These sets of wafers could only be examined under reflection THz-TDS based techniques. In this case, the wafer is placed in standard THz-TDS set-up at 45° and vertical to the collimated incident THz beam, which was reflected off the surface unfocused, at a spot size of ~43 mm. The second batch of dielectric coated wafers, with photoresist (PR) or nitride deposition (ND), is able to transmit though the THz radiation. Here, the wafer is again placed vertical and perpendicular to the THz beam which is focused with the aid of an off-axis parabolic mirror to a spot size of ~3 mm. This second set enabled performance of Visible Pump/THz Probe measurements in transmission with a continuous wave (CW) multi-line visible Argon-ion laser as the pump source operating at a center wavelength of $\lambda$=514 nm with an average power of 450 mW/cm2. In this case, the visible pump is not time-resolved, so that we are not probing the carrier dynamics but the response of the photo-excited carriers to the THz E-Field.

It is preferable to have the pump spot larger than the probe spot so that the density of photo-induced carriers by the pump is uniform over the area sampled by the probe.

As will be apparent to one of ordinary skill in the art, the pump wavelength that is employed is in the appropriate wavelength that is required to preferentially photo-excite the defects at the boundary of the high κ dielectric.

Theoretical Model

The theoretical model is based on the Drude theory which is briefly revisited below. The Preliminary Theoretical model discussed below neglects any diffusive effects of the pump beam while the Advanced Analysis discussed below incorporates the effects of diffusion and the effective medium approximation. Also provided below is an outline of the method for evaluating the number of interface traps in the interfacial layer.

The Drude Model

The Drude model is based on the classical equations of motion of an electron in an optical electric field and gives the simplest theory of optical constants of materials, where the major contribution to the dielectric function is through free carriers. See, Ashcroft N. W. and Mermin N. D., "Solid State Physics," Brooks Cole, New York, N.Y. (1976) and Bohren C. F. and Huffman D. R., "Absorption and Scattering of light by Small Particles," John Wiley and Sons, New York, N.Y. (1983), each of which is incorporated herein by reference.

Figures 7A, 7B:
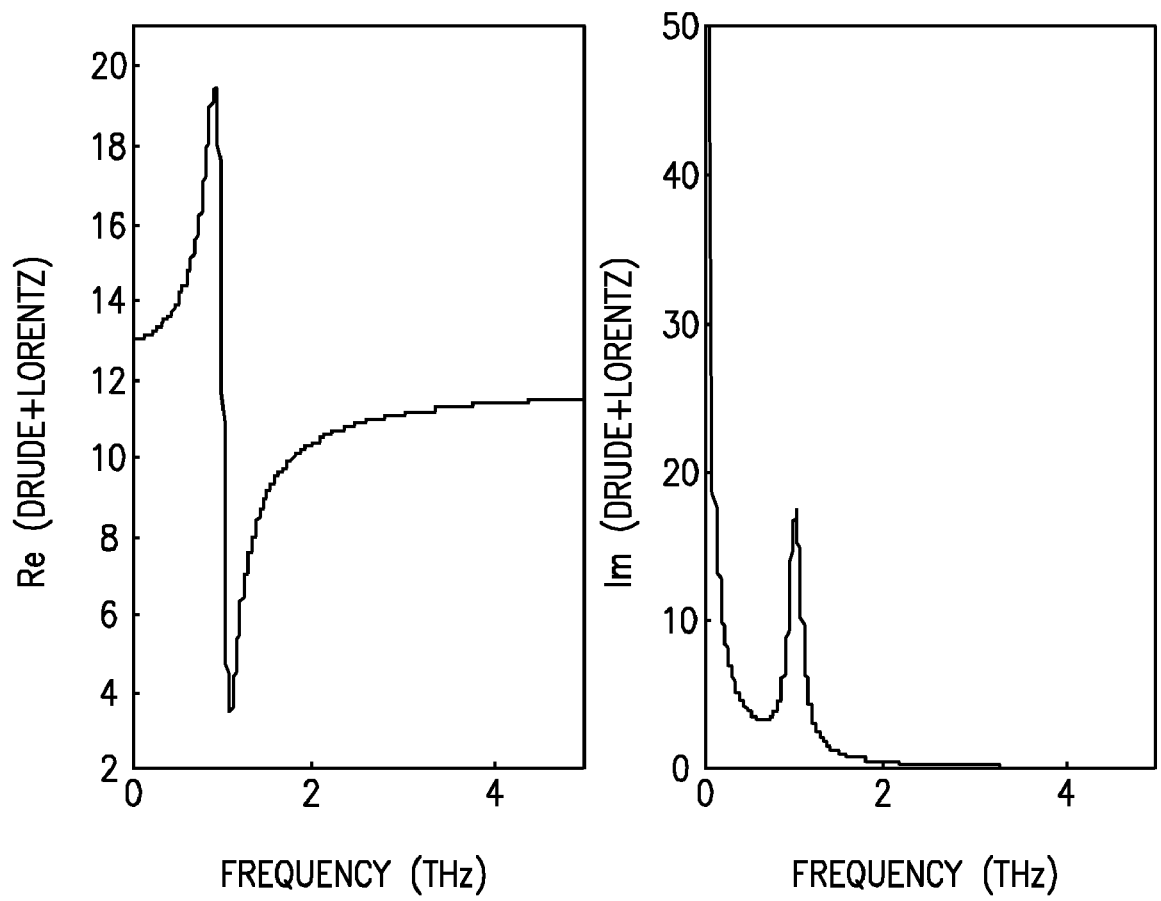
FIG. 7 shows the combined Drude and Lorentz responses for the real and imaginary parts of the dielectric function, with FIG. 7A showing the real part, and FIG. 7B showing the imaginary part.

FIG. 6 shows real and imaginary parts of the dielectric function for p-type silicon for the Drude model (FIGS. 6A and 6B, respectively) and for the Lorentz model (FIGS. 6C and 6D respectively). The Drude parameters were $N^p$=1.46× $10^{16}$ cm$^{-3}$, $\tau$=1×$10^{-12}$s corresponding to $\mu_p$=140 cm$^2$/V/s for $m*_p$=0.38 $m_o$. Plasma frequency=1.759 THz. Lorentz parameters for m=1 are, $\Omega_m$=10 THz, $\Gamma_m$=1 THz, $\omega_m$=1 THz. The Lorentz absorption is introduced to show how it would affect overall response. FIGS. 7A and 7B show the combined Drude and Lorentz response for the real and imaginary parts, respectively, of the dielectric function.

This model is not limited to metals (since they have inherent free carriers), even nonconductors show a free electron type behavior at sufficiently high frequencies. See, Philip H. R. and Ehrenrich H., "Optical properties of semiconductors," Phys. Rev., 129, 1550-1560 (1963), incorporated herein by reference.

Impurities in semiconductors, which release either free electrons or free holes, also give rise to optical transitions below the minimum band gap that are characteristic of the Drude theory.

Preliminary Modeling involving the method of Transformed Impedances

According to the Drude model, the frequency dependent dielectric constant of a material is given by, $$n^2 \% = (n + ik)^2 = \varepsilon(\omega) = \varepsilon_\infty - \frac{\omega_p^2}{\omega^2 + i\frac{\omega}{\tau}} \quad (4.1)$$

(Zielbauer J. and Wegener M., "Ultrafast optical pump THz-probe spectroscopy on silicon," Appl. Phys. Lett., 68, 1223-1225 (1996), incorporated herein by reference) where n is the real and k is the imaginary part of the complex index of refraction, $\varepsilon_\infty$ is the dielectric constant of the material at high frequencies, $1/\tau$ is the collision frequency and $\omega_p = (4\pi Ne^2/m_{\textit{eff}})^{1/2}$, N, e, $m_{\textit{eff}}$ are the plasma frequency, number density, electronic charge and effective mass of the free carriers (electrons or holes) respectively. Separating the real and imaginary parts of the above equation we obtain, $$\left.\begin{array}{l} \varepsilon_r = \varepsilon_\infty - \dfrac{\omega_p^2}{\omega^2 + \dfrac{1}{\tau^2}} \\[2ex] \varepsilon_i = \dfrac{\omega_p^2}{\omega^3 \tau + \dfrac{\omega}{\tau}} \end{array}\right\} \quad (4.2)$$

Two different types of methods can be used for the subsequent analysis of the experimental data. The first is the transfer matrix method and the second is the impedance matching method.

Abeles Method of Transfer Matrices

By using the transfer matrix method, the linear transmission at normal incidence through n' layers, $n_0$ being the first medium is given by, $$T = \left| \frac{2n_0}{M_{11}n_0 + M_{12}n_0 n' + M_{21}n_0 + M_{22}n_0 n'} \right|^2 \quad (4.3)$$

where $M_{ij} = M_{n+1} M_{n+2} \ldots M_{n'}$ and $$M_{dielectric} = \begin{pmatrix} \cos\delta_d & \dfrac{i\sin\delta_d}{n_d} \\ in_d \sin\delta_d & \cos\delta_d \end{pmatrix} \quad (4.4)$$

where $\delta_d = n_d k_0 d_d$ and the symbols have their usual meanings with $d_n$ being the thickness of medium n. Further details following this method of analysis are disclosed in Altan H., Sengupta A., Federici J. F., Grebel H. and Pham D., "Estimation of defect characteristics of $HfO_2$ and $SiO_2$ on p-type silicon substrates using THz spectroscopy," J. Appl. Phys., under review (2005), attached hereto as Appendix A and incorporated herein by reference. However, one of the main drawbacks of this approach is it restricts any dispersion of the material properties and inherently makes the paraxial assumption of $\sin\theta \cong \tan\theta \cong \theta$ which is not always true in real-world applications. To overcome such hindrances, the impedance matching approach is considered.

Method of Impedance Matching

The impedance of a plane wave traveling in a medium of relative permeability $\mu_r$ and dielectric constant $\varepsilon_r$ is $$Z = \sqrt{\frac{\mu_r \mu_0}{\varepsilon_r \varepsilon_0}} = Z_0 \sqrt{\frac{\mu_r}{\varepsilon_r}} \quad (4.5)$$

Since for our case, $\mu_r = 1$, the impedance can be written as $Z = Z_0/n$ where n is the refractive index of the material. When optical radiation is incident on an interface between materials having different impedances, then the amount of optical energy that is transmitted is related to the impedances of all the materials under concern. Since the faces of the wafers under investigation are very flat and parallel, and the light source is coherent, the method of transformed impedances (see, Ramo S., Whinnery J. R. and Van Duzer R., "Fields and Waves in Communication Electronics," Wiley, New York, N.Y. (1993) is used to calculate the transmission through such a multilayer structure.

Figure 11B:
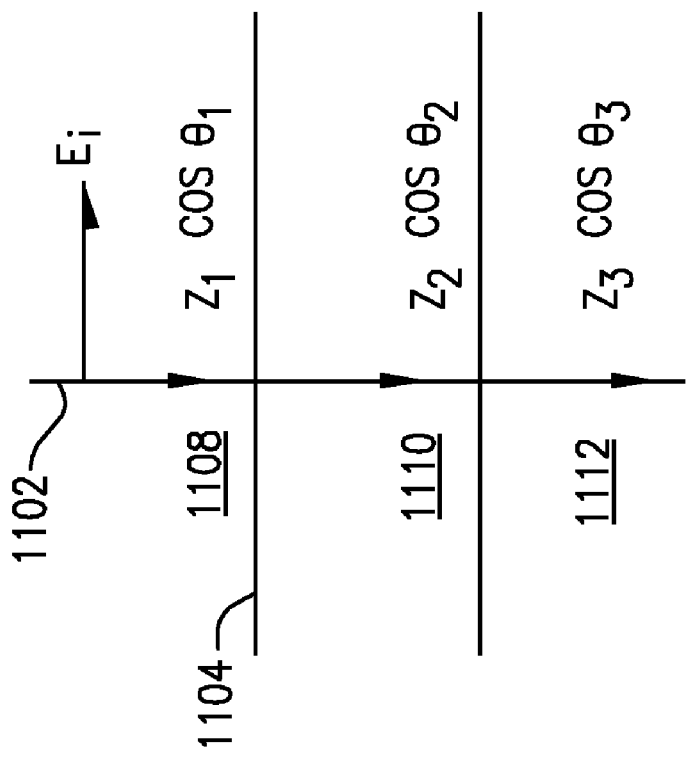
FIG. 11B is a schematic representation of a wave passing through a dielectric slab in accordance with another embodiment of the invention.
Figure 11A:
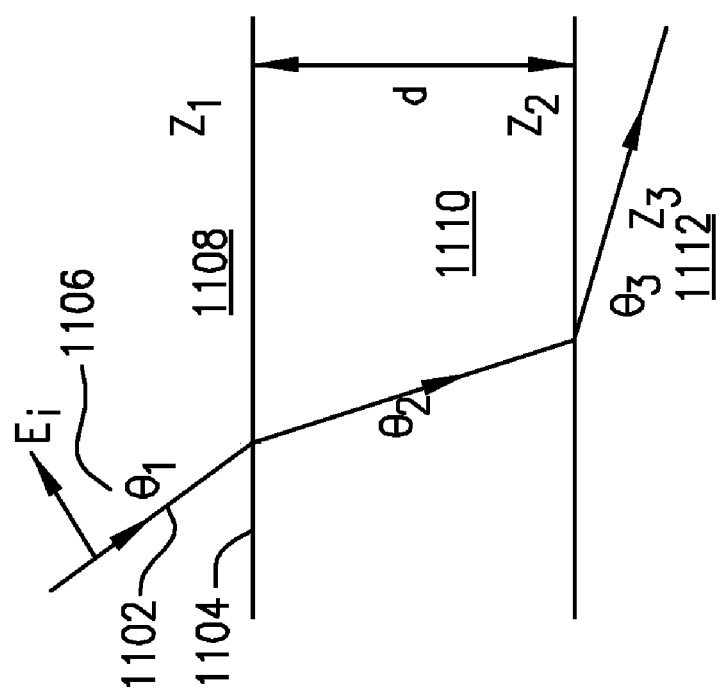
FIG. 11A is a schematic representation of a wave passing through a dielectric slab in accordance with an embodiment of the invention.

FIG. 11 shows waves passing through a dielectric slab. FIG. 11A shows waves 1102 incident at an acute angle 1106 to a surface 1104 through which the waves are refracted and transmitted. FIG. 11B shows a normal impedance structure equivalent to the structure shown in FIG. 11A. Three layers are shown: layer 1108 having impedance $Z_1$, layer 1110 having impedance $Z_2$, and layer 1112 having impedance $Z_3$. Considering the three layer structure of FIG. 11, the effective impedances of media 1108, 1110, and 1112 are $$Z_1' = Z_1 \cos\theta_1 Z_0 \cos\theta_1/n_1$$

$$Z_2' = Z_2 \cos\theta_2 = Z_0 \cos\theta_2/n_2$$

$$Z_3' = Z_3 \cos\theta_3 = Z_0 \cos\theta_3/n_3 \quad (4.6)$$

See, Davies C. C., "Lasers and Electro-Optics," Cambridge University Press, Cambridge, UK (1996).

It can be shown that the reflection and transmission coefficients of the structure are exactly the same as shown in FIG. 11B for normal incidence where the effective thickness of layer 2 1110 is given by $d' = d\cos\theta_2$.

The transformed impedance of medium 3 1112 at the boundary between media 1 and 2 is, $$Z_3'' = Z_2' \left( \frac{Z_3' \cos k_2 d' + iZ_2' \sin k_2 d'}{Z_2' \cos k_2 d' + iZ_3' \sin k_2 d'} \right) \quad (4.7)$$

where $k_2$ is the wave number in a medium 2. The transmission is given by, $$T = \frac{2Z_3''}{Z_3'' + Z_1'} \quad (4.8)$$

For the unpumped and pumped structures which have five and three interfaces respectively, Equation 4.7 has been used sequentially starting at the last optical surface and working back to the first. The respective impedances are given in Equations 4.9 (a) and (b).

$$Z_6'''' = Z_2 \left( \frac{Z_6'''' \cos k_2 d_2' + i\sin Z_2' \sin k_2 d_2'}{Z_2' \cos k_2 d_2' + i\sin Z_6'''' \sin k_2 d_2'} \right) \quad (4.9a)$$

-continued $$Z_4''' = Z_2 \left( \frac{Z_4'' \cos k_2 d_2' + i \sin Z_2' \sin k_2 d_2'}{Z_2' \cos k_2 d_2' + i \sin Z_4'' \sin k_2 d_2'} \right) \quad (4.9b)$$

It should be noted that for the differential transmission (multiline visible Argon pump-THz probe) measurements, it is assumed that the layer underneath the oxide is a single, homogeneous layer. This is justified since our probing wavelength is much larger than the thickness of the p+ layer. In addition to this, one can assume that the p+ layer is so heavily doped that the electron hole concentration near the surface is far greater than deep into the substrate (wherein "deep" here refers to a depth of about 1 micrometer) since the intermediate P+ layer is so heavily doped. Limiting the free-carrier interactions to only the interface allows us not to make any assumptions on the thickness of the layer either. One can further simplify the analysis by observing the time domain plots (shown in FIG. 16) and noting that the only change observed in the THz transmission is a reduction in its amplitude due to its photoexcitation rather than a phase change. Hence, it can be said that the change in the index of refraction due to photo-excitation affects only the imaginary part of the refractive index. Thus, $$\Delta n = i \Delta k = i \frac{\Delta \varepsilon_i}{2n} \quad (4.10)$$

where $\Delta \varepsilon_i$ is the change in the imaginary part of the dielectric constant of the material due to photo-excitation which is obtained from, $$\Delta \varepsilon_i = \frac{\left( 4\pi \Delta N \frac{e}{m_{eff}} \right) \cdot \Delta \tau}{\omega \cdot [1 + (\omega \Delta \tau)^2]} \quad (4.11)$$

where $\Delta N$ and $\Delta \tau$ are the changes in the carrier concentration and scattering time respectively due to photoexcitation.

Following this method of analysis, the obtained Drude model fits to linear reflection and transmission scans and it is seen that results agree with experimental measurements. To obtain analytical fits to the differential experiments in order to estimate the number of photoexcited defect states, the analysis was done separately for the pumped and unpumped states and then the difference was normalized to the unpumped measurements. This is justified since pumping was with a CW laser source. This method also allows one to extract the values of the mobility in the interfacial layer from the carrier scattering time.

The value of the frequency independent characteristic optical constants of the materials of the different layers of the wafer that was used in the calculations is shown in Table 4.1.

TABLE 4.1

Optical Properties of Materials (N is the doping concentration)

| | Silicon (Si) | $SiO_2$ | $HfO_2$ | $Si_3N_4$ | Photo-resist |
|---|---|---|---|---|---|
| Refractive Index (n) | 3.42[i] | 1.5[28] | 2.1[ii] | 2.1[iii] | 1.4[iv] |
| Abs. Coeff. ($cm^{-1}$) | $2.06 \times 10^{-16} \times N^v$ | ~0.00 | $4.89 \times 10^{3vi}$ | 3.891 | 11 |

TABLE 4.1-continued

Optical Properties of Materials (N is the doping concentration)

| | Silicon (Si) | $SiO_2$ | $HfO_2$ | $Si_3N_4$ | Photo-resist |
|---|---|---|---|---|---|
| Mass ratio ($m_{eff}/m$) | 0.26 (e), 0.38 (h) | — | — | — | — |

Advanced Modeling with Diffusion and Effective Medium Approximation

Diffusive Effects of the Photoexcited Carriers

Figure 12:
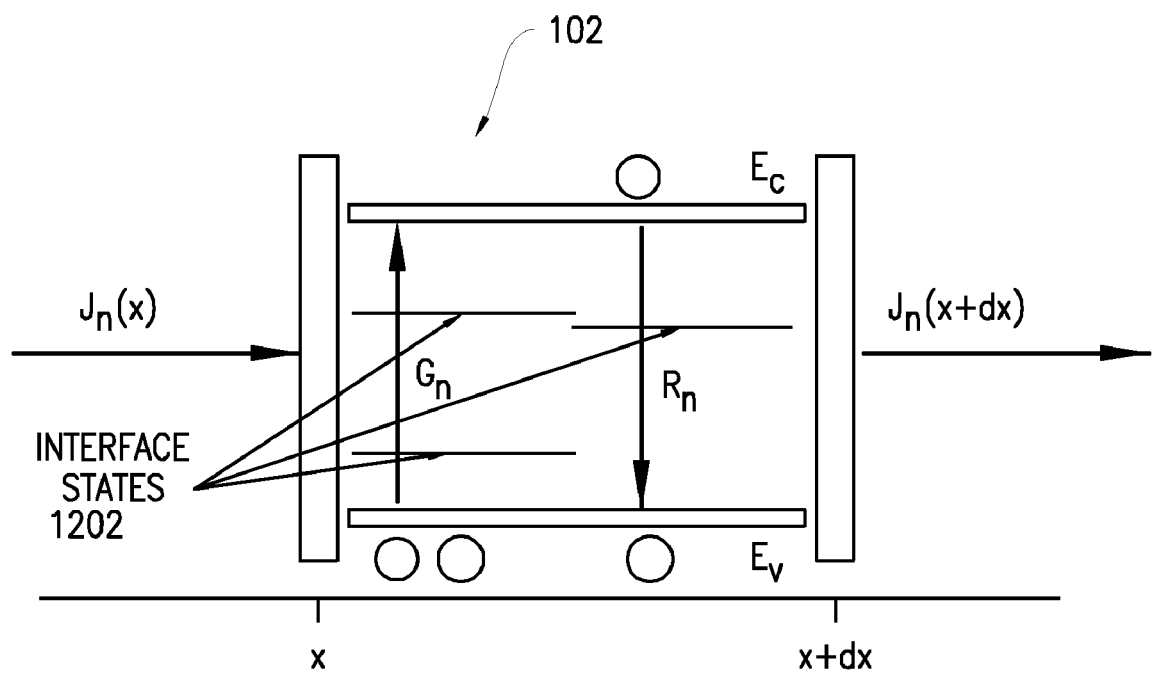
FIG. 12 is a schematic representation of recombination and generation processes at a dielectric/substrate interface in accordance with an embodiment of the invention.
Figure 13A:
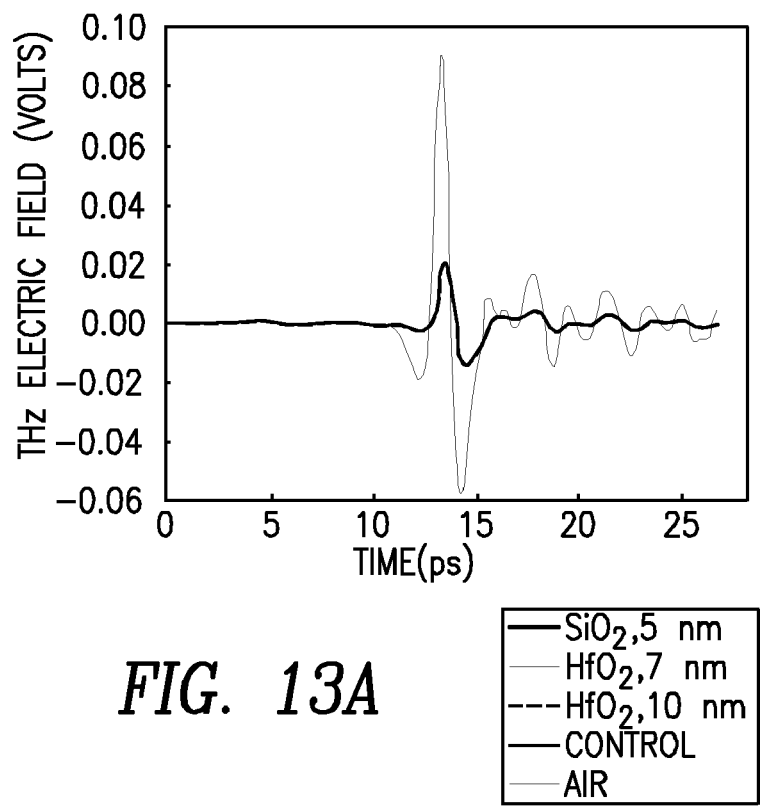
FIG. 13A is a graph of reflected electric field strength versus time at a wafer in accordance with an embodiment of the invention.
Figure 13B:
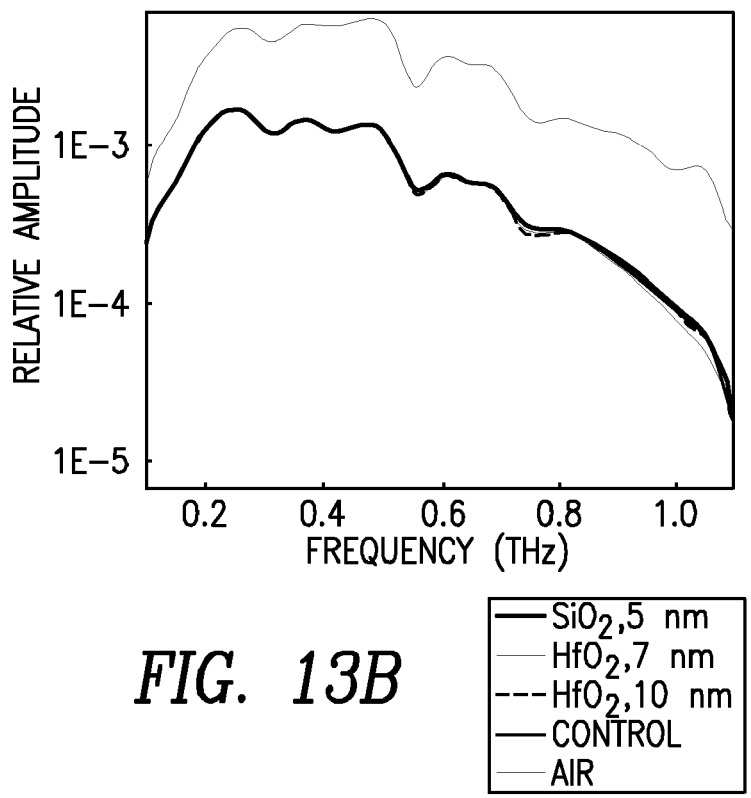
FIG. 13B is a graph of the Fourier transform of the graph of FIG. 13A.
Figure 13C:
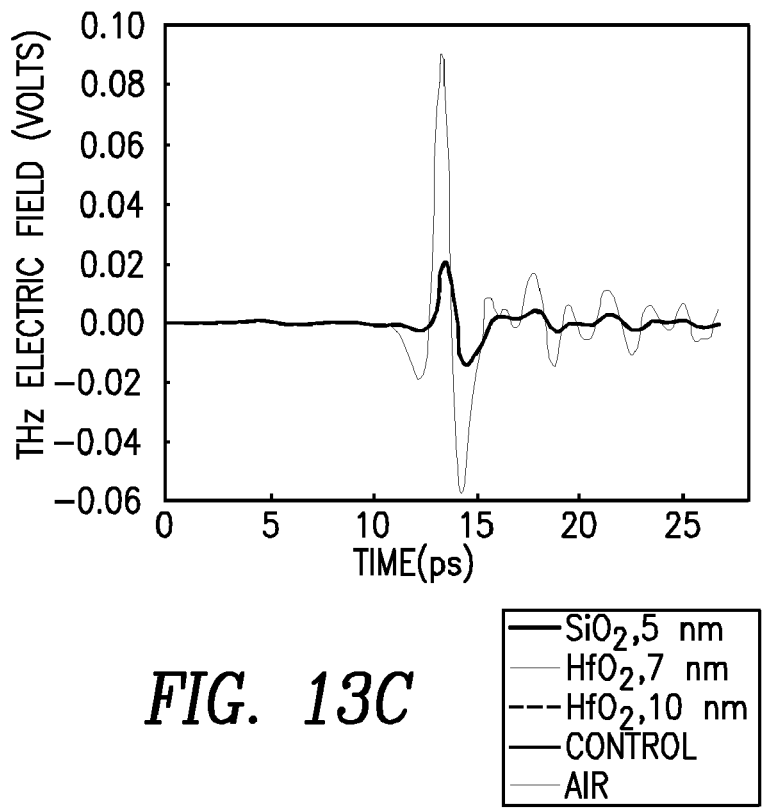
FIG. 13C is a graph of reflected electric field strength versus time at a wafer in accordance with another embodiment of the invention.
Figure 13D:
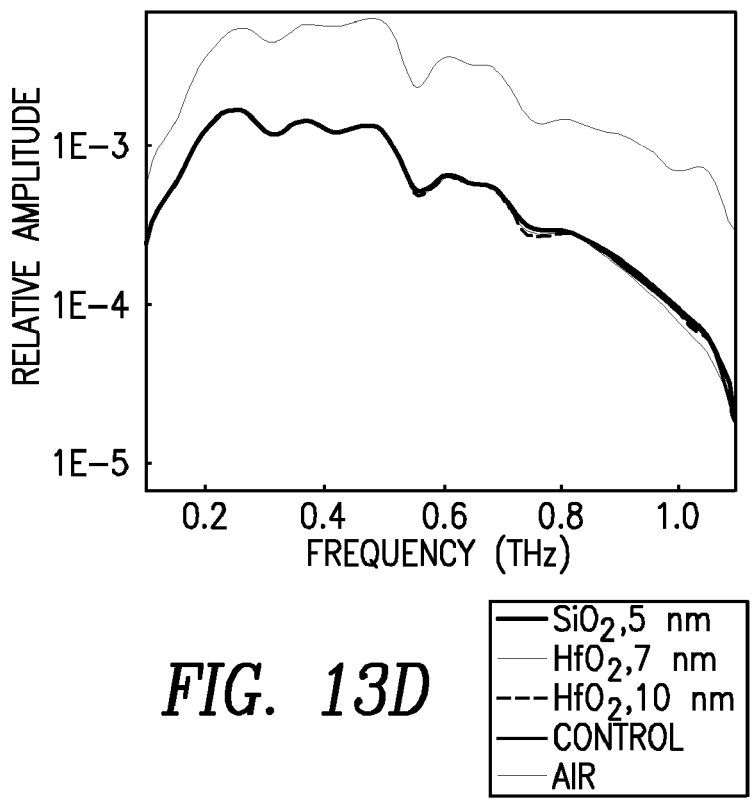
FIG. 13D is a graph of the Fourier Transform of the graph of FIG. 13c.

FIG. 12 shows electron currents and possible recombination and generation processes in sample 102. The interface states have also been shown to demonstrate their position at the gate dielectric/substrate interface which takes part in the recombination of the CW radiation under photoexcitation. The continuity equation describes that a change in carrier density with time is due to the difference in the incoming and outgoing flux of carriers taking into account generation and recombination processes. The flow of carriers and recombination and generation rates are shown in FIG. 12. With reference to FIG. 12, Jn(x) is the current density of the charge carriers (n) at position x in the sample 102. Jn(x+dx) is the current density of charge carriers at position x+dx in the sample 102. Ec is the conduction band energy level, and Ev is the valance band energy level. Gn is the generation rate of charge carriers and Rn is the combination rate.

When the pump laser (CW Argon laser) is incident on the front face of the sample, there is a decrease in the intensity of the beam according to Beer-Lambert's law, $I = I_0 e^{-\alpha z}$ where the absorption coefficient of the medium is $\alpha$ and I is the intensity of the radiation at a distance z from the point where the intensity of the radiation is $I_0$. This concentration gradient of the optical energy due to the optical pump beam accounts for the variation in the number of photoexcited carriers generated at the surface of the interfacial layer than in the bulk of the same layer. The carriers generated at the surface will gradually diffuse into the layer.

In the following analysis, diffusive effects in the $HfO_2$ layer, the interfacial layer between $HfO_2$ and p+ Silicon layer and the p+ Silicon layer have been accounted for since the calculations show that the effects of the pump beam will not go beyond 50 nm of the p+ Silicon layer and there is no evidence in literature to show that the pump beam will produce carriers in the photoresist layer.

Once the steady state has been reached, the diffusion equation for the photoexcited carriers takes the form, $$D_n \frac{d^2 n_n(x)}{dx^2} = \frac{n_n(x) - n_n(0)}{\tau_n} \quad (4.12)$$

See, Boltaks B. I., "Diffusion in Semiconductors," Academic Press, New York, N.Y. (1963).

In the above equation, the subscript n refers to electrons, where $D_n$ is the diffusion coefficient of the electron and $\tau_n$ refers to the electron scattering time. A similar equation can be written for the positive carriers or holes. Assuming that one is interested in the region x>0 and the fact that the concentration of the carriers has to decrease as one goes deep into the medium, the solution to this second order differential equation is, $$n_n(x) = Ae^{-\frac{x}{L_n}} \qquad (4.13)$$

where $L_n = \sqrt{D_n \tau_n}$ is the characteristic diffusion length of the electron in a particular medium and $n_n(x)$ is the concentration of the electrons at a distance x from the surface of the medium. Further, the diffusion coefficient is related to the mobility of the carriers in a particular layer by the Einstein relations. See, Zukic M., Torr D. G., Span J. F. and Torr M. R., "Vacuum ultraviolet thin films. 1: Optical Constants of HaF-BaF$_2$, CaF$_2$, LaF$_3$, MgF$_2$, Al$_2$O$_3$, HfO$_2$ and SiO$_2$ thin films," Appl. Opt., 29, 4284 (1990). Hence, it is understood that due to the diffusion, there is a non-uniform distribution of the carriers along different points of the same layer, that is, along the direction of propagation of the pump beam through the sample.

This effect of diffusion of the carriers is accounted for in the analysis by incorporating the right hand side of Equation 4.13 in the imaginary part of the dielectric constant of a particular layer given in Equation 4.2. Since one is interested in the number of defects in the interfacial layer between the gate dielectric and the p+ Silicon layer, one assumes that there is a change in the diffusion coefficient of the carriers in this particular layer due to photoexcitation. This is justified as more carriers having energies in the THz range are generated when the laser light is incident on the sample which is also evident from the experimental measurements as shown in FIG. 16. From the figure, it is observed that when the sample is photoexcited, the amount of THz radiation transmitted is much less compared to similar linear measurements.

However, there is the issue of the dielectric constant of the interface layer which must be calculated to a reasonable degree of accuracy to correctly estimate the actual number of defect states in the interfacial layer between the gate dielectric and the substrate and this forms the subject of the next section.

Estimation of Dielectric constant using Effective Medium Approximation

The dielectric response of a heterogeneous material and the limits to the amount of microstructural information that can be drawn from it can be understood when it is recalled that electrodynamics deals with macroscopic observables that are basically averages of their microscopic counterparts. The solution to the effective dielectric problem therefore, involves two distinct steps: first, the electrostatic problem is solved exactly for the given microstructure to obtain the local electric field e(r) and dipole moment p(r) per unit volume at every point in space; secondly, these microscopic solutions are averaged to obtain their macroscopic counterparts. See, Van Kranendonk J. and Sipe J. E., "Foundations of the macroscopic electromagnetic theory," Prog. Opt., 15, 246-350 (1977); Aspnes D. E., "Optical properties of thin films," Thin Solid Films, 89, 249-262 (1982).

The Lorentz-Lorentz (LL), Maxwell-Garnett (MG) and Bruggeman (BG) effective medium approximation models are simple effective medium theories that represent a heterogeneous dielectric mixture by a single parameter. See, Grandqvist C. G. and Hunderi O., "Optical properties of ultrafine gold particles," Phys. Rev. B, 16, 3513-3534 (1977). Hence, they represent a natural first approximation to model the dielectric constant of the interfacial layer between the substrate and the gate dielectric material. The situation is similar to that of a binary disordered material consisting of two materials having dielectric functions $\in_1(v)$ and $\in_2(v)$ with concentrations (volume fractions) of $f_1$ and $f_2$[27]. See, Van Kranendonk J. and Sipe J. E., "Foundations of the macroscopic electromagnetic theory," Prog. Opt., 15, 246-350 (1977); Spanier J. E. and Herman I. P., "Use of hybrid phenomenological and statistical effective medium theories of dielectric functions to model the infrared reflectance of porous SiC films," Phys. Rev. B., 61, 10437-10450 (2000); Schuler A., Ellenberger C., Oelhafen P., Haug C. and Brenn R., "Optical properties of titanium containing amorphous hydrogenated carbon films," J. Appl. Phys., 87, 4285-4292 (2000).

In the LL approximation, which was developed to describe point polarizable entities of polarizability α embedded in vacuum with $\in_h = 1$, the effective dielectric constant is given by, $$\frac{\varepsilon_{eff} - 1}{\varepsilon_{eff} + 2} = f_{HfO_2,SiO_2} \frac{\varepsilon_{HfO_2,SiO_2} - 1}{\varepsilon_{HfO_2,SiO_2} + 2} + f_{Si} \frac{\varepsilon_{Si} - 1}{\varepsilon_{Si} + 2} \qquad (4.14)$$

The MG approximation assumes that the different materials involved consist of regions large enough to possess their own dielectric identity. If the host dielectric medium (for our case, Silicon) has a dielectric function of $\in_{Si}$ the effective dielectric constant is given by, $$\frac{\varepsilon_{eff} - \varepsilon_{Si}}{\varepsilon_{eff} + 2\varepsilon_{Si}} = f_{HfO_2,SiO_2} \frac{\varepsilon_{HfO_2,SiO_2} - \varepsilon_{Si}}{\varepsilon_{HfO_2,SiO_2} + 2\varepsilon_{Si}} \qquad (4.15)$$

The BG expression allows the effective medium itself to act as the host medium and in this approximation, the effective dielectric constant of the interfacial layer for the wafers under investigation is given by, $$f_{HfO_2,SiO_2} \frac{\varepsilon_{HfO_2,SiO_2} - \varepsilon_{eff}}{\varepsilon_{HfO_2,SiO_2} + 2\varepsilon_{eff}} + f_{Si} \frac{\varepsilon_{Si} - \varepsilon_{eff}}{\varepsilon_{Si} + 2\varepsilon_{eff}} = 0 \qquad (4.14)$$

where in all the above expressions, HfO$_2$ and SiO$_2$ refer to the gate dielectric of the particular wafer under consideration. Equation 4.14 approximates an aggregate or random mixture microstructure where HfO$_2$ and SiO$_2$ are inserted into the effective medium itself. Since the interfacial layer in our case is not a guest-host configuration, which is typical to the description of nanomaterials using LL or MG models, the BG approximation has been used to model the experimental data. See, Kalnin J. R. and Kotomin E., "Modified Maxwell-Garnett and Lorentz-Lorentz equations for the effective transport coefficients in inhomogeneous media," J. Phys. A: Math. Gen., 31, 7227-7234 (1998); Levy O. and Stroud D., "Maxwell-Garnett theory for mixtures of anisotropic inclusions: Application to conducting polymers," Phys. Rev. B., 56, 8035-8056 (1997).

It should be remembered that the application of the effective medium approximation is justified since the size of the non-homogeneities (~few nm) is well below the wavelength of the probing radiation (~hundreds of microns). Also, as a first order approximation, it has been assumed that the interfacial layer is free of any voids.

The incorporation of diffusion effects and the Bruggeman Effective Medium approximation gives the most accurate results for modeling the results of the differential measurements as has been shown below.

Evaluation of the number of Interface Traps

Assuming that the recombination time of the carriers in the interfacial layer between $HfO_2$ or $SiO_2$ and p+ Silicon layer to be the same, the following expression can be written for the number of interface traps, $$\frac{\sigma(HfO_2)N_{IT}(HfO_2)}{\sigma(SiO_2)N_{IT}(SiO_2)} = \frac{\Delta N(HfO_2)}{\Delta N(SiO_2)} \quad (4.15)$$

where $\sigma$ is the photon absorption cross-section, $N_{IT}$ is the number of interface traps and $\Delta N$ is the number of photoexcited states. See Appendix A hereto.

Experimental Results and Analysis

Linear Time Domain Measurements

As mentioned above, two types of experiments were performed on the samples. This section shows the results of the linear THz transmission experiments.

FIG. 13 shows results of reflection measurements on the gate dielectric wafers. FIG. 13A shows the time domain scans; FIG. 13B shows the corresponding Fourier transforms having a $Si_3N_4$ coating as the topmost layer; and FIGS. 13C and 13D show time-domain and frequency-domain representations, respectively, for the photoresist coated wafers. The dips at 0.56 and 0.78 THz are due to water vapor absorption. FIG. 13 shows the results of the linear time domain scans in reflection mode on the different wafers. As is seen, the experiment was performed in such a manner that the THz beam arrived on all the samples at the same time as without them.

Figure 14:
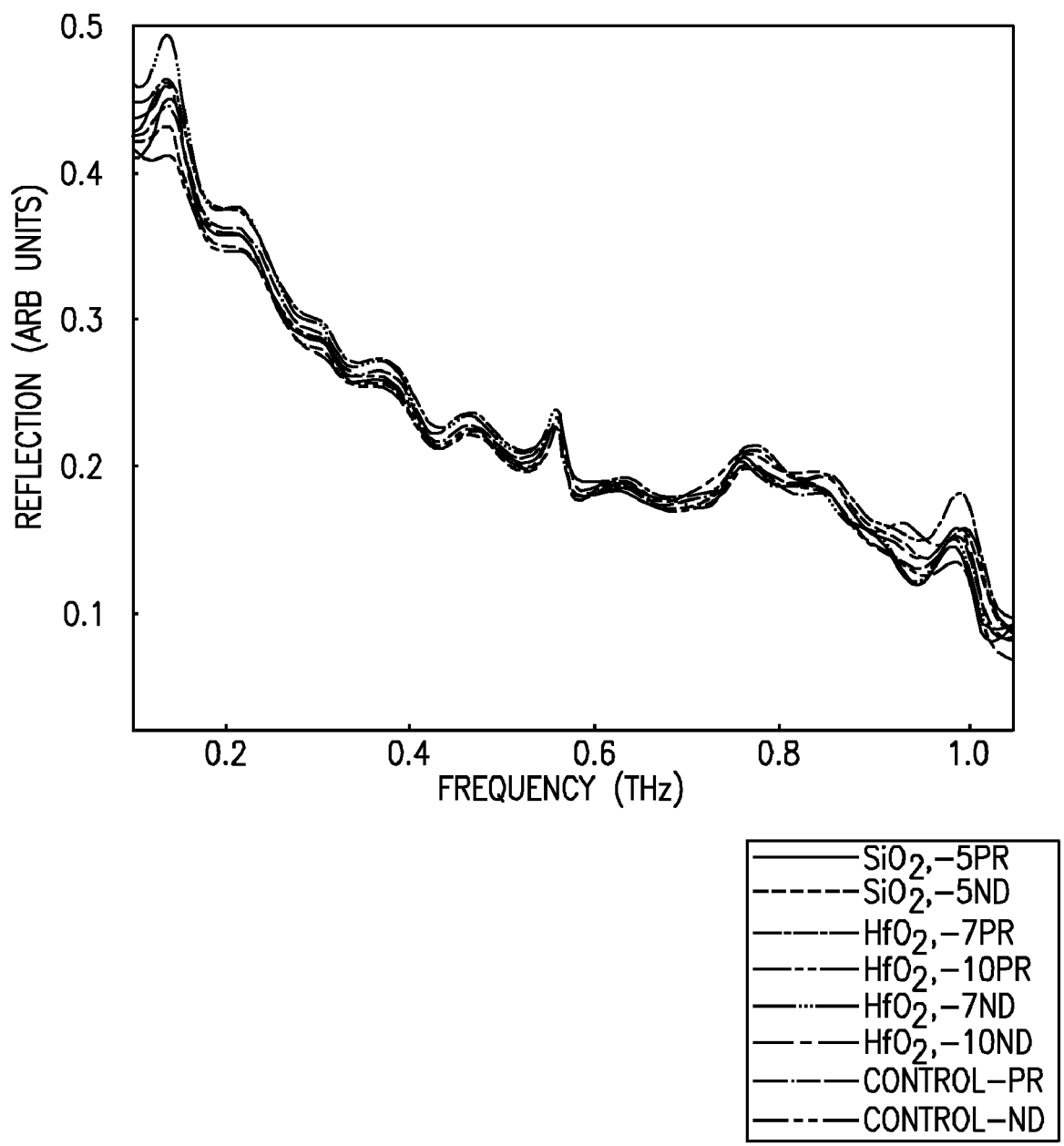
FIG. 14 is a graph of the reflection spectrum of wafers having various gate dielectric materials.

As is observed from these results, the different types of wafers cannot be distinguished under such measurements. FIG. 14 shows the reflection spectra of wafers having various gate dielectrics. The numbers in the legend for each of the wafers refers to the thickness of the gate dielectric layer in nanometers. The expression "PR" means the wafer was photoresist coated, and the expression "ND" means the wafer was Si3N4 coated. It is noted that the difficulty in distinguishing measurements mentioned above regarding FIG. 13 is also reflected in the reflection spectra shown in FIG. 14. The reflection spectra have been normalized to the spectra of the gold mirror.

Figure 15A:
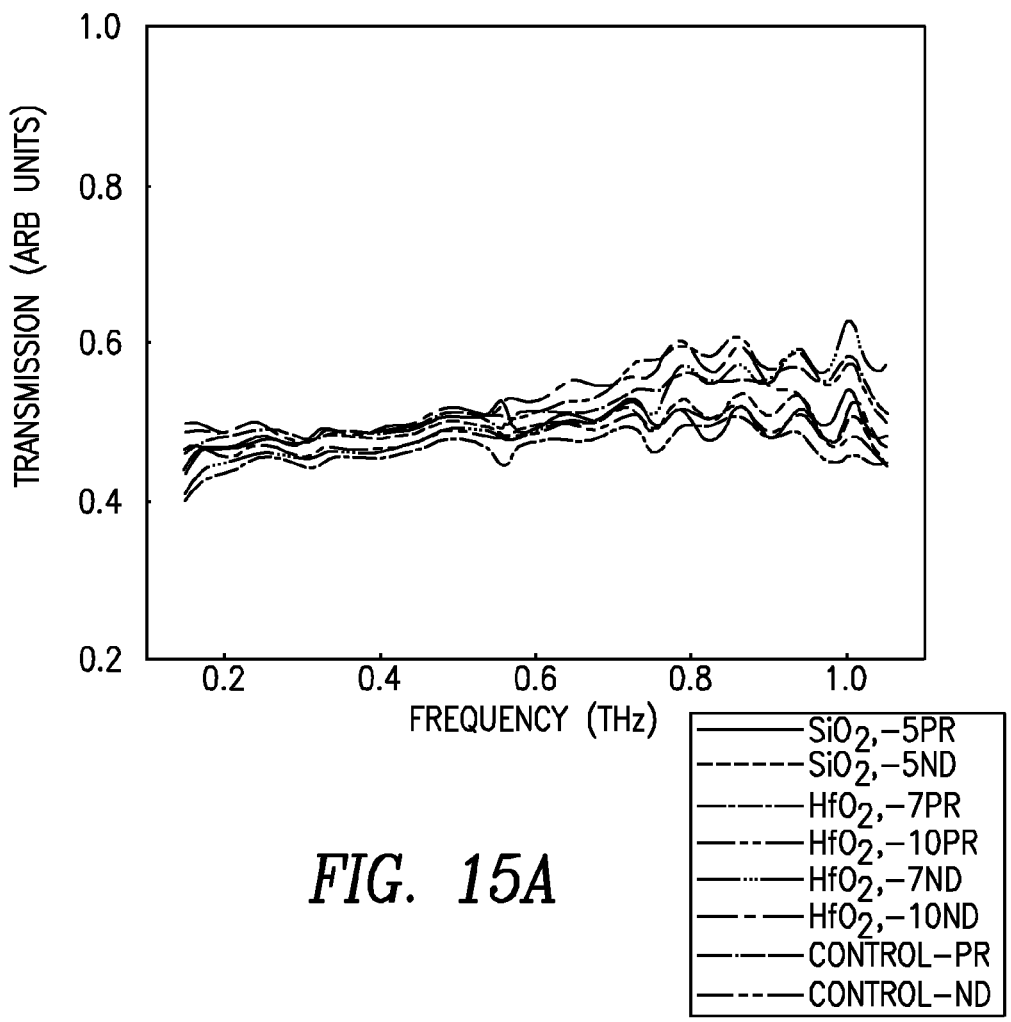
FIG. 15A is a graph of the transmission spectrum of various wafers in accordance with an embodiment of the invention.
Figure 15B:
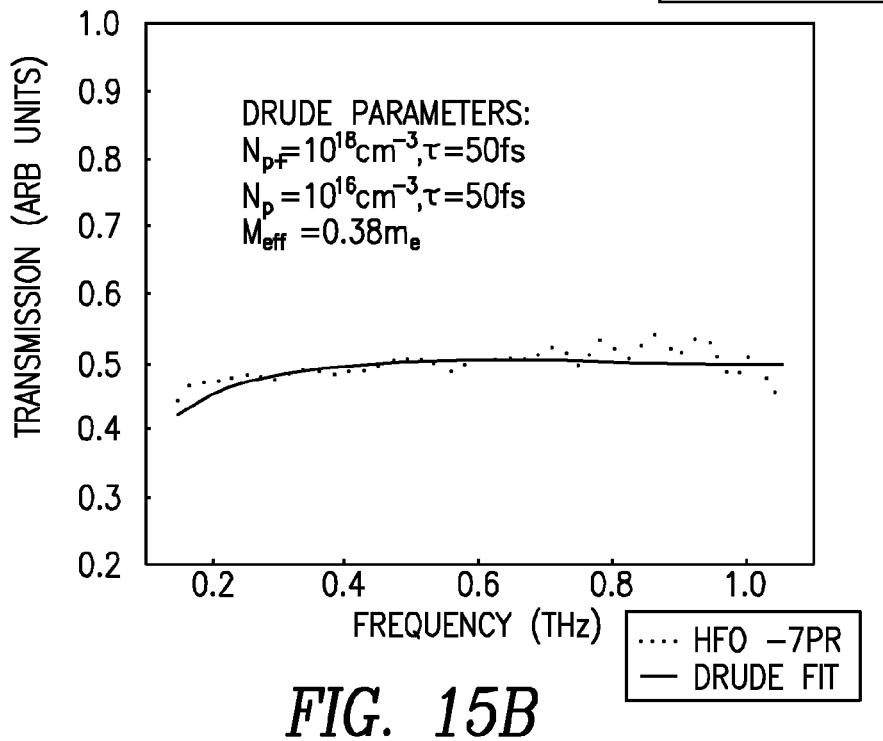
FIG. 15B is graph of a Drude fit of transmission data for a wafer with a 7 nanometer layer of hafnium oxide coated with photoresist in accordance with an embodiment of the invention.

FIG. 15A shows the results of the transmission measurements on the same set of wafers, and FIG. 15B shows the results of the Drude model fit using the impedance matching approach as discussed above.

Once again, it is seen that the various wafers appear similar under linear transmission measurements. The Drude parameters obtained from the fit, namely, the carrier concentration $N_{p+}$, $N_p$ and the respective scattering times $\tau$ match closely with the specifications provided by the manufacturer and have been used for subsequent calculations in the analysis of the data obtained from differential measurements.

It is observed from the graphs shown in FIGS. 14 and 15 that the scatter is more in the case of transmission measurements which can be attributed to the fact that the spot size of the THz beam is only 3 mm for transmission measurements compared to 45 mm for reflection measurements. This results in the transmission experiments to be more sensitive to film non-homogeneities, surface roughness and other physical attributes.

Optical Pump-THz Probe Measurements

Figure 16A:
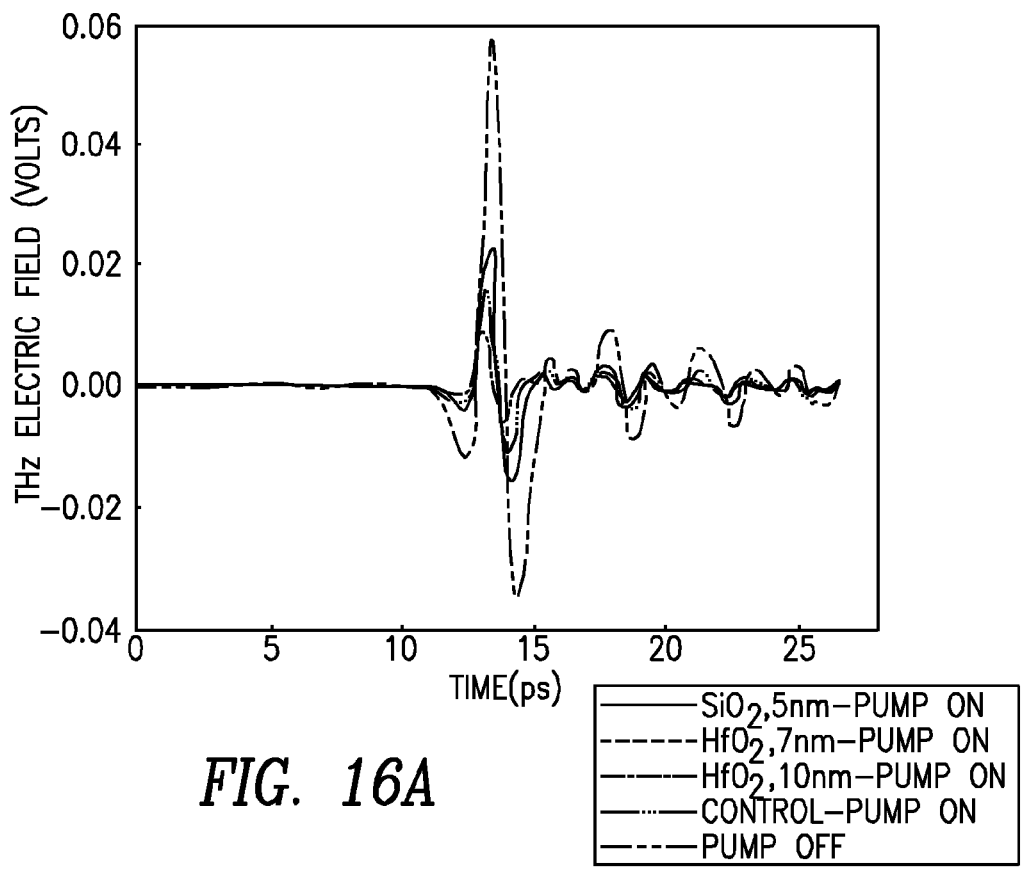
FIG. 16A is a plot of electric field against time for wafer in accordance with one embodiment of the invention.
Figure 16B:
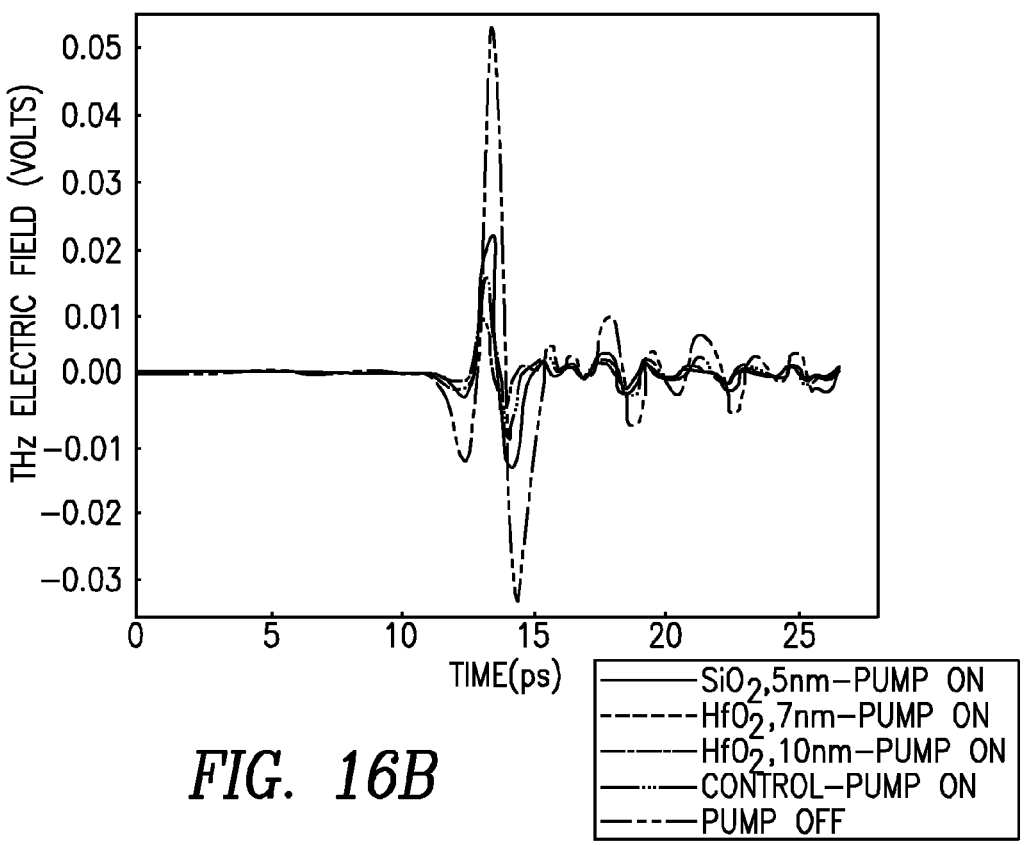
FIG. 16B is a graph of electric field against time for a wafer in accordance with another embodiment of the invention.

FIG. 16 shows the time domain plots of optical pump-THz probe measurements on the set of wafers having various respective dielectric layers. As mentioned earlier, the optical pump was a multi-line visible CW Argon laser at 514 nm with an intensity of 0.5 W/cm². FIG. 16A shows plots for wafers having $Si_3N_4$ coatings; and FIG. 16B shows plots for wafers having photoresist coatings.

It can be seen from the graphs that even though, the wafers all looked similar under linear reflection and transmission measurements, there are pronounced differences between them under optical pump-THz probe measurements. Also, the most dominant effect observed is a change in amplitude of the THz waveform which suggests that the change in transmission is mainly due to the imaginary part of the dielectric constant as mentioned above.

Figure 17:
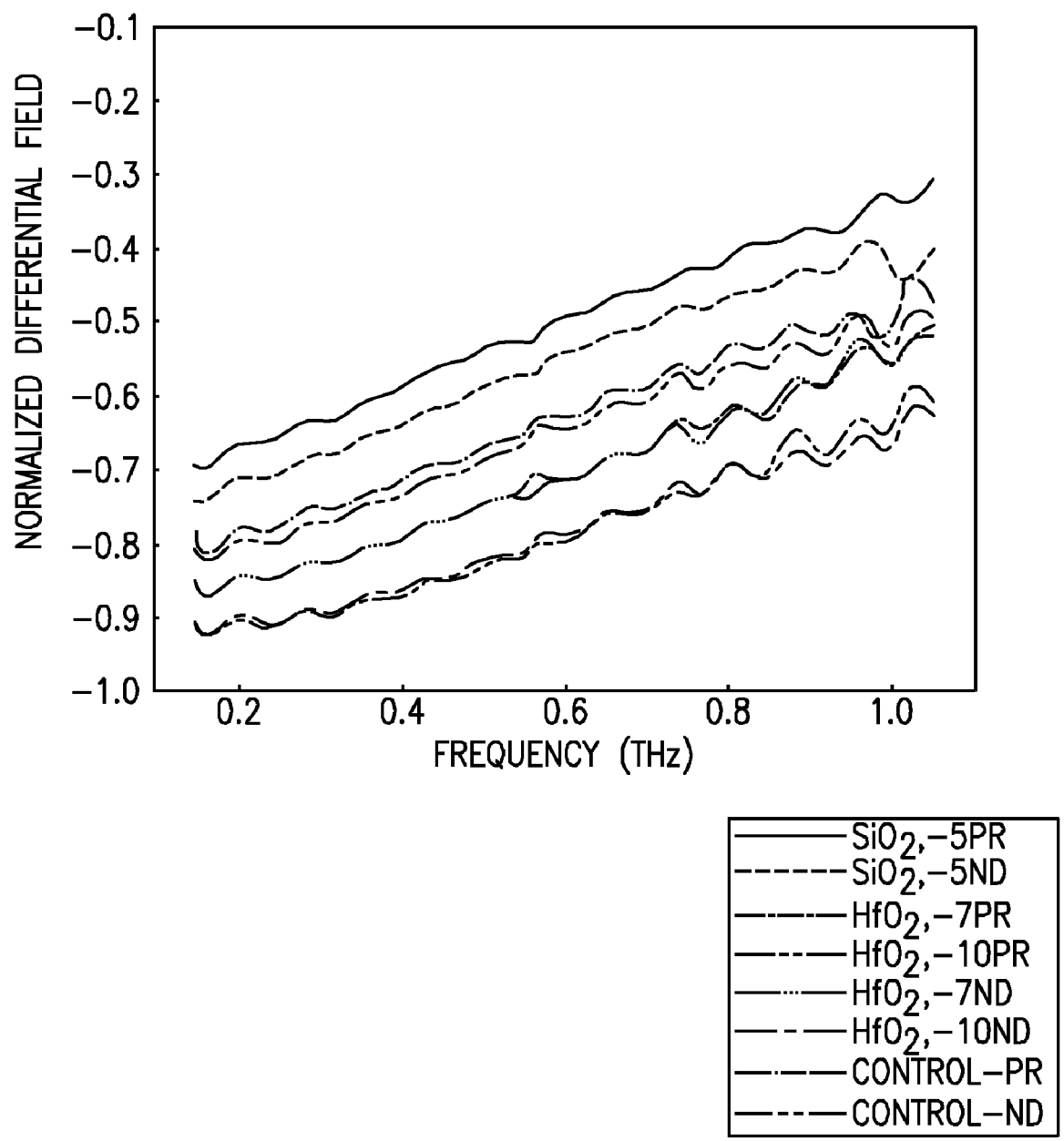
FIG. 17 is a graph including plots of normalized electric field for various wafers in accordance with an embodiment of the invention.

FIG. 17 shows differential plots for various wafers under visible light excitation using a power level of 0.5 W/cm². Clear differences can be observed between the different sets of wafers. The differential plots as shown in FIG. 17 have been constructed by taking the difference of the experimental measurements for the case when the pump beam was on to the case when the pump beam was off and then this difference was normalized to the pump beam off situation. This calculation is expressed in the following equation, $$\text{Normalized Differential Field, } D_{THz} = \frac{E_{pump\ on} - E_{pump\ off}}{E_{pump\ off}} \quad (4.16)$$

It is observed from the plots that the differences between the wafers are more evident under visible pump-THz probe measurements. It is even possible to distinguish between the photoresist coated and the $Si_3N_4$ coated wafers. However, the current technique cannot distinguish between the wafers having either 7 nm or 10 nm thick $HfO_2$ layers.

Analysis of Experimental Data

Preliminary modeling using the method of transfer matrices gives results as shown in Table 4.2. The details of the calculations have been shown in Appendix A. As is seen from the table, the number of photoexcited carriers is too large. Though it is possible that carriers are generated at the rate of $10^{18}$/second, diffusive effects will reduce the number of carriers that is seen by the THz probe pulse. At the same time, this model assumed that the scattering time of the carriers in the interfacial layer for both the $SiO_2/Si$ and the $HfO_2/Si$ interface is the same. Since the model did not account for any difference in the scattering time of the carriers (it was assumed to be 200 fs), no estimate of the mobility in the interfacial layers of the different wafers was made.

TABLE 4.2

| Parameters extracted by the transfer matrix method | |
|---|---|
| Wafer | No. of photoexcited states(cm⁻³) |
| Silicon Dioxide(PR) | $3 \times 10^{16}$ |
| Silicon Dioxide(ND) | $8 \times 10^{16}$ |
| Hafnium Dioxide(PR) | $3 \times 10^{17}$ |
| Hafnium Dioxide(ND) | $4.8 \times 10^{17}$ |
| Control(PR) | $1.7 \times 10^{17}$ |
| Control(ND) | $2 \times 10^{17}$ |

Figure 18A:
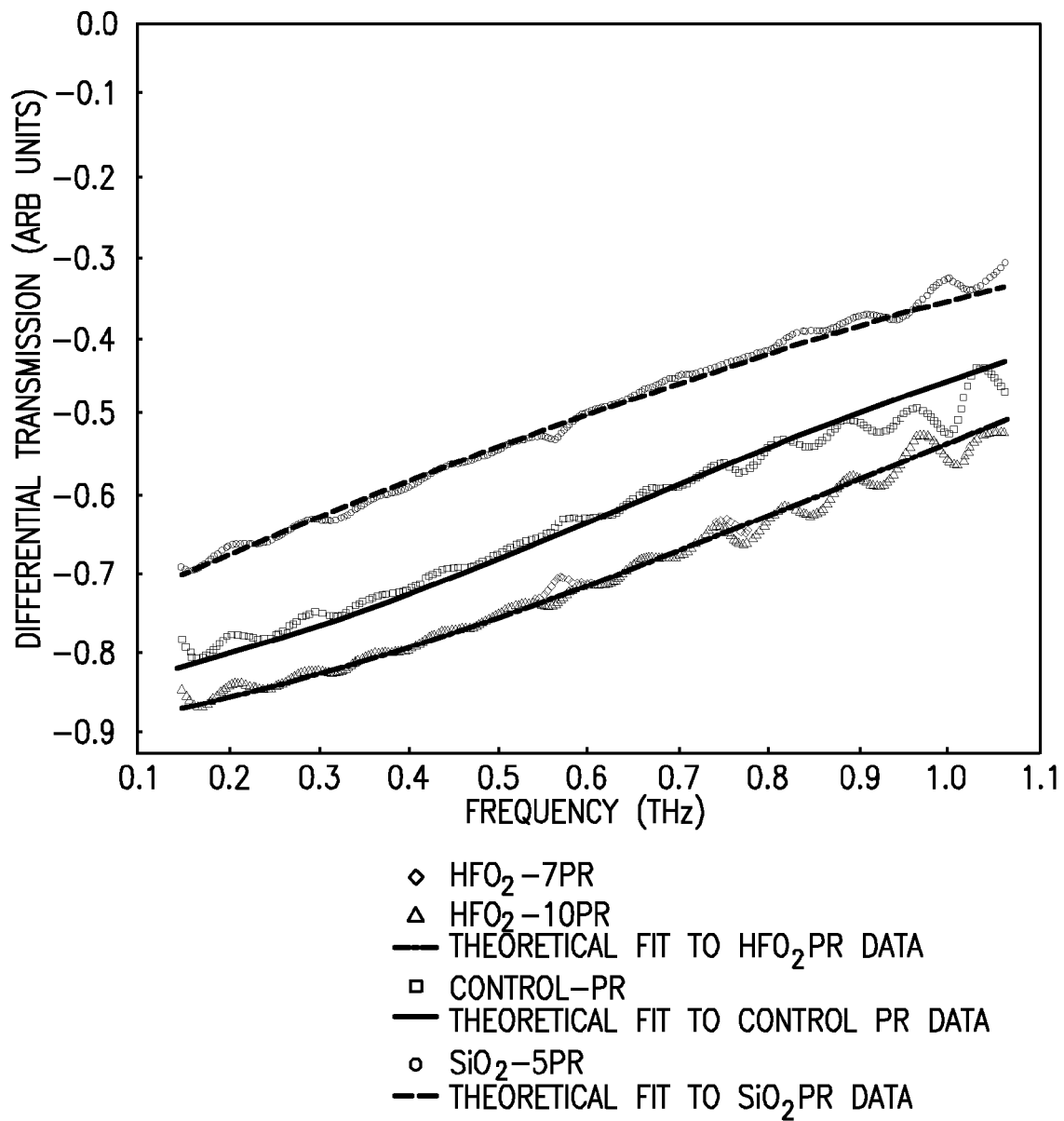
FIG. 18A is a graph showing differential plots and theoretical fits versus frequency for photoresist coated samples.
Figure 18B:
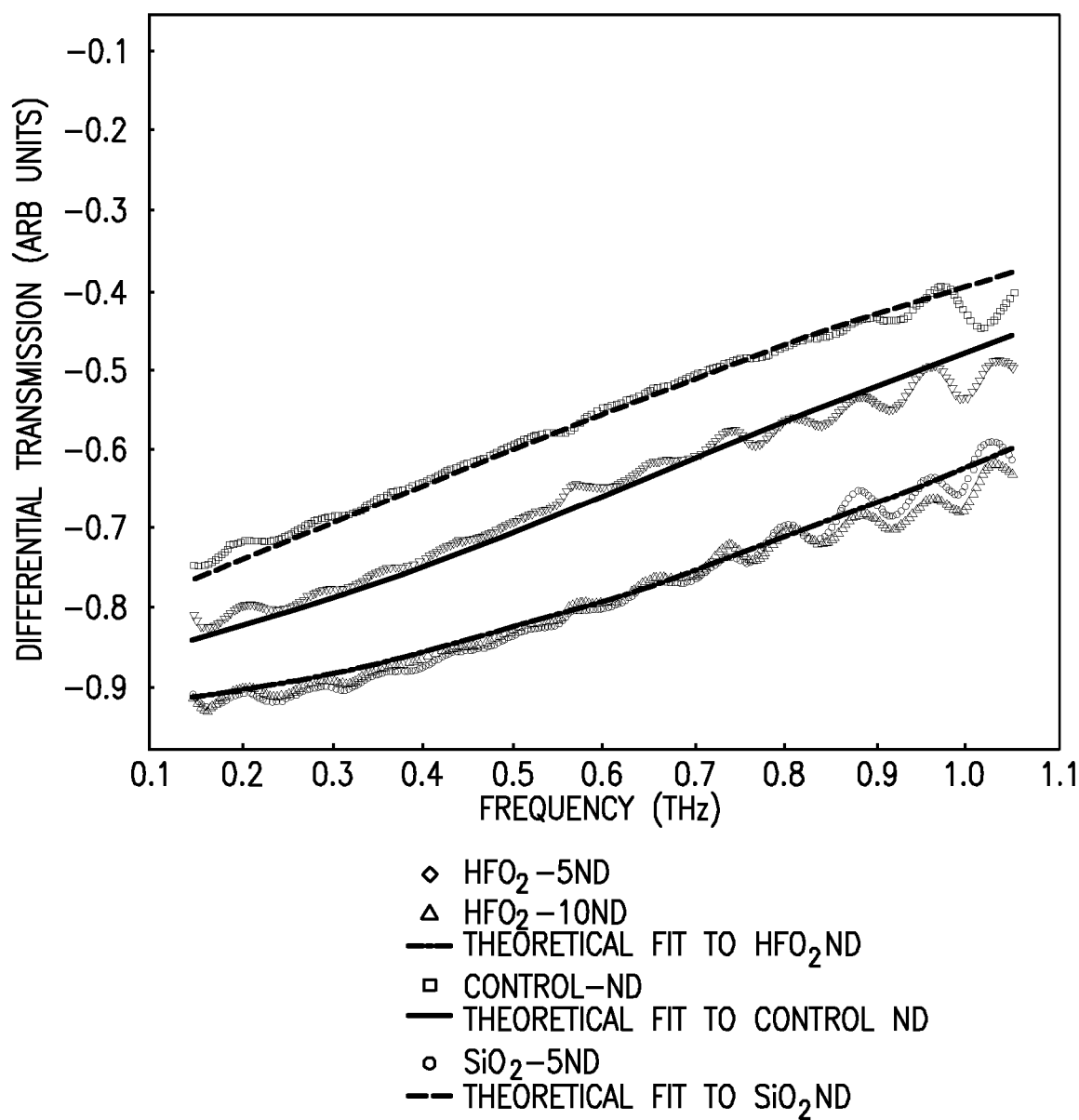
FIG. 18B is a plot of differential plots and theoretical fits versus frequency for samples coated with $Si_3N_4$.

The more general modeling involving the impedance matching approach incorporated the variation of the scattering time for the different layers and it gave slightly better estimates of the number of photoexcited defect states. Additionally in accordance with Equation 4.11, the algorithm automatically calculated the scattering times for the different interfacial layers (namely $HfO_2$/Silicon and $SiO_2$/Silicon)

from which an estimate of the mobility of the interfacial layer was also possible by using the equation, $$\mu_{e,p} = \frac{e\tau_{e,p}}{m_{e,p}}, \quad (4.17)$$

where the subscripts e and p refer to electrons and holes respectively. FIG. 18 shows differential plots and theoretical fits for photoresist-coated samples (FIG. 18A) and $Si_3N_4$ coated samples (FIG. 18B). It can be seen that using the simple analysis as described for impedance matching hereinabove, accurate fits are generated by changing the carrier concentration and scattering times for the different wafers. The theoretical fits to the experimentally obtained data for visible pump-THz probe measurements shown in FIG. 18 and the corresponding number of defect states and extracted mobility values have been tabulated in Table 4.3. The number of photoexcited defect states for the $HfO_2$/Silicon interface is found to be at least ten times more than for the $SiO_2$/Silicon interface. However, the number is too high considering the fact that our pump beam was continuous. At the same time, the results of the number of defect states are off by at least a few orders of magnitude from the expected theoretical values. See, Wilk G. D., Wallace R. M. and Anthony J. M., "High κ gate dielectrics: current status and materials properties considerations," J. Appl. Phys., 89, 5243-5275 (2001), incorporated fully herein by reference. This is expected because Equation 4.15 assumes that the scattering times are similar for all the wafers.

TABLE 4.3

Defect States and Mobility for different wafers(preliminary analysis)

| Wafer | No. of defect states($cm^{-3}$) | Mobility ($cm^2$/V-s) |
|---|---|---|
| Silicon Dioxide(PR) | $3.0 \times 10^{14}$ | 450 |
| Silicon Dioxide(ND) | $8.0 \times 10^{14}$ | 430 |
| Hafnium Dioxide(PR) | $3.0 \times 10^{15}$ | 240 |
| Hafnium Dioxide(ND) | $4.8 \times 10^{15}$ | 210 |
| Control(PR) | $1.7 \times 10^{15}$ | 225 |
| Control(ND) | $2.0 \times 10^{15}$ | 210 |

Figure 19A:
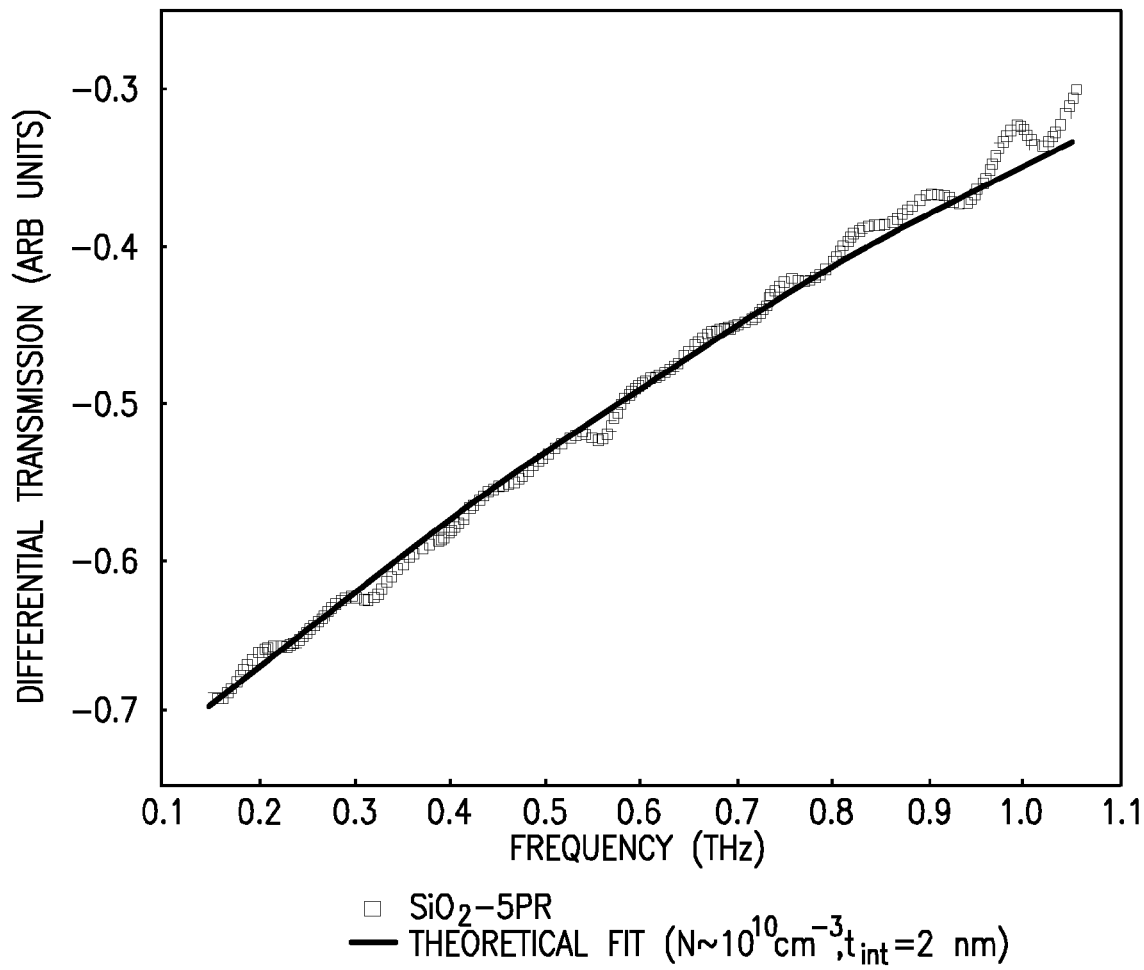
FIG. 19A is a graph of differential transmission versus frequency for a wafer in accordance with one embodiment of the present invention.
Figure 19B:
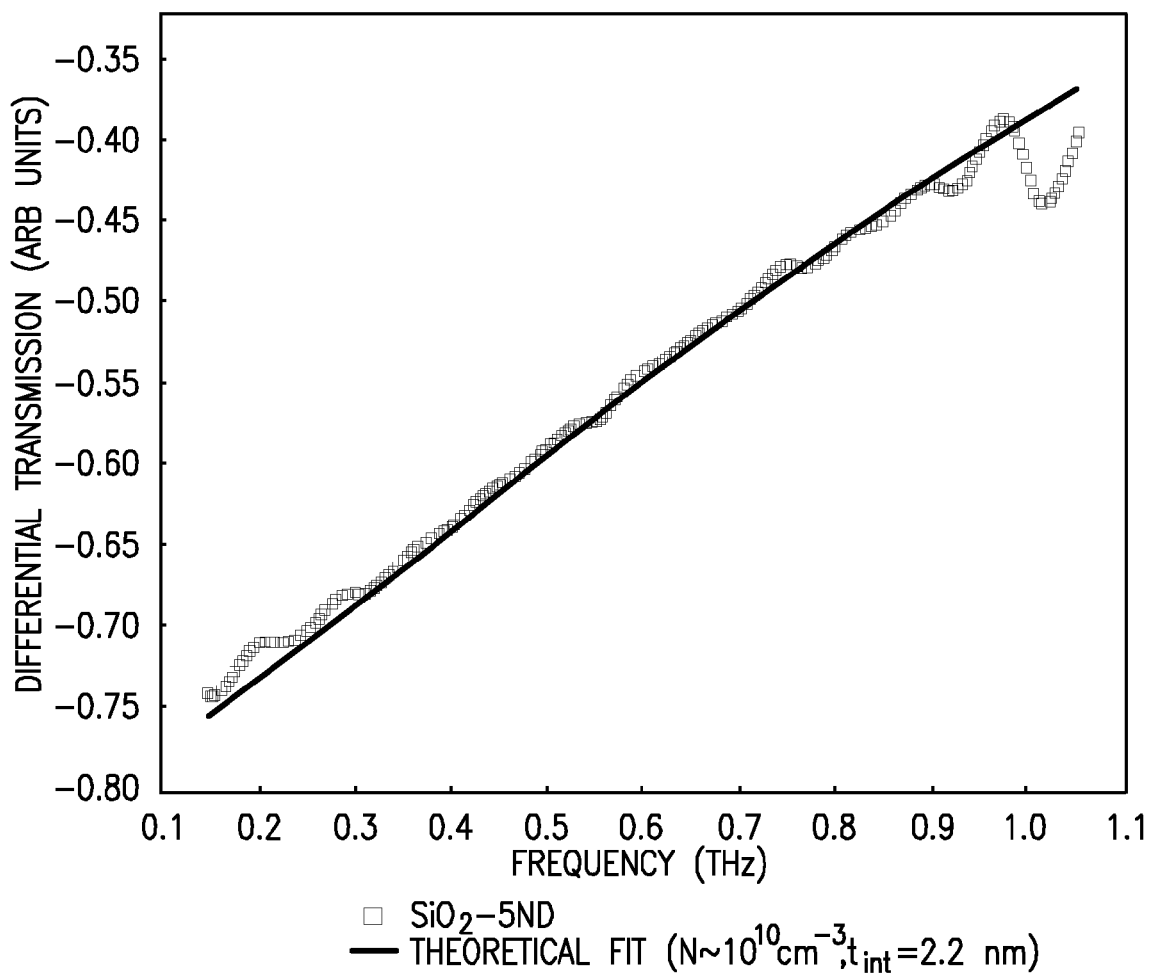
FIG. 19B is a graph of differential transmission versus frequency for a wafer in accordance with another embodiment of the present invention.
Figure 19C:
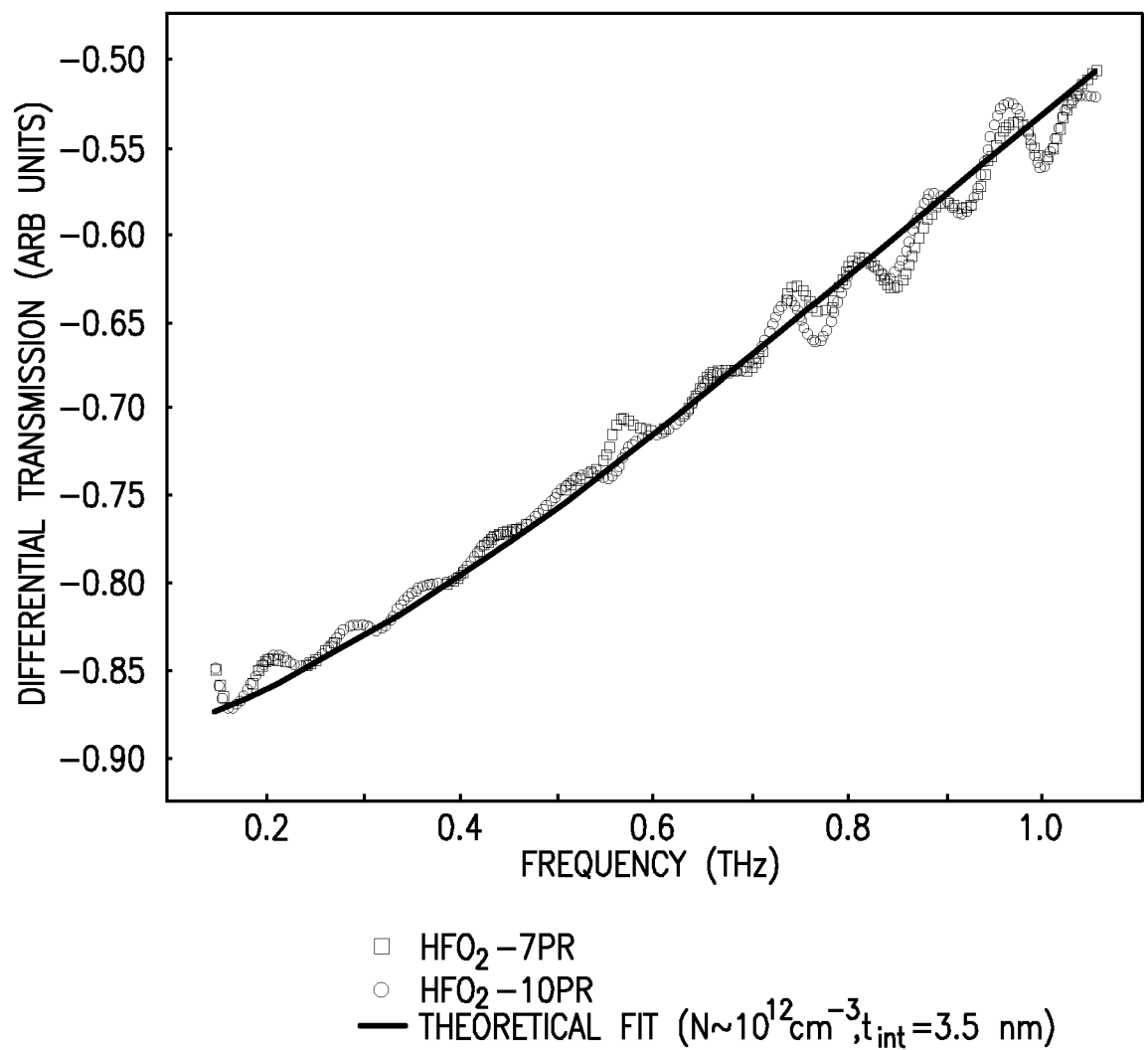
FIG. 19C is a graph of differential transmission versus frequency for a wafer in accordance with yet another embodiment of the present invention.
Figure 19D:
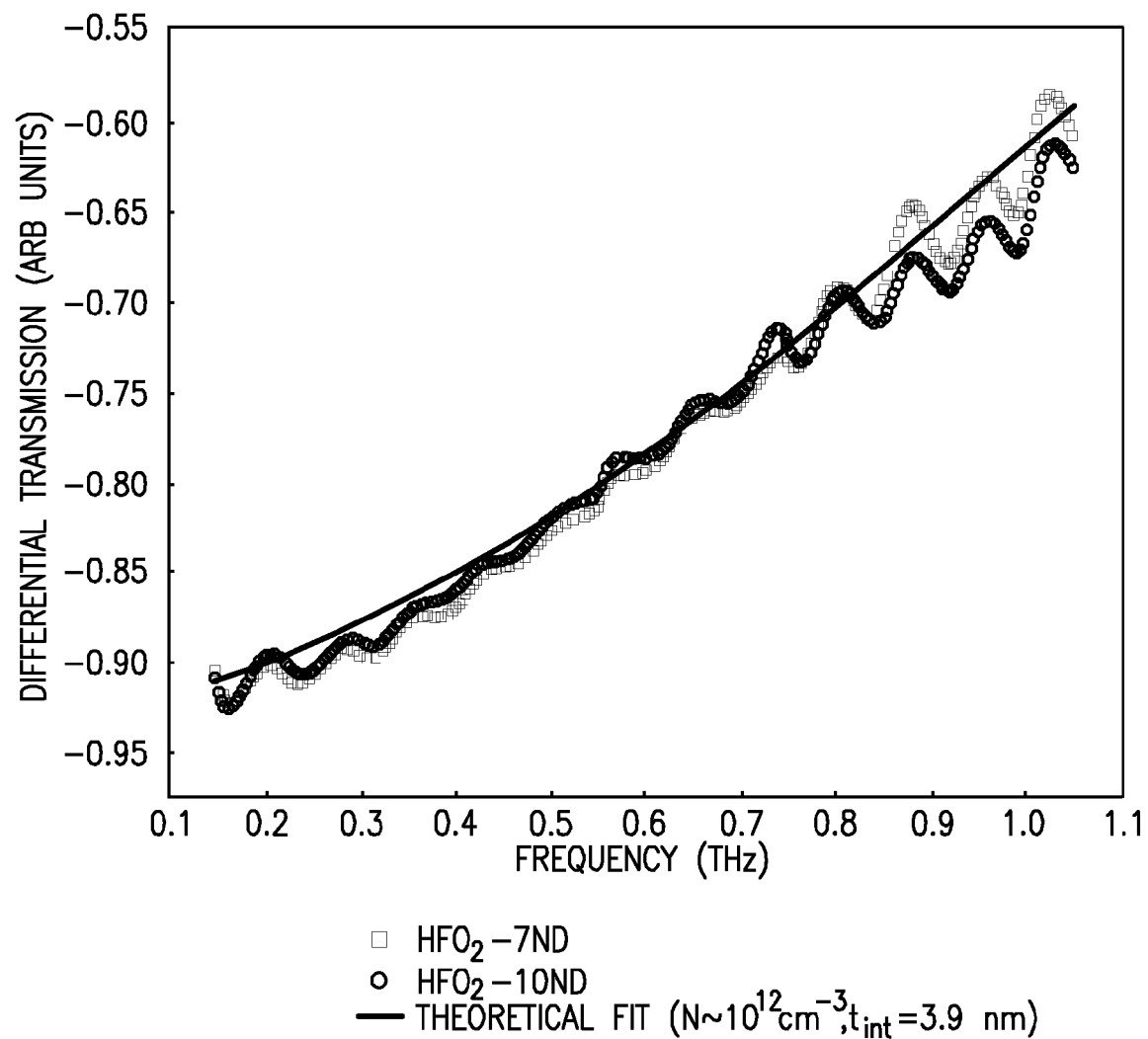
FIG. 19D is a graph of differential transmission versus frequency for a wafer in accordance with yet another embodiment of the present invention.
Figure 19E:
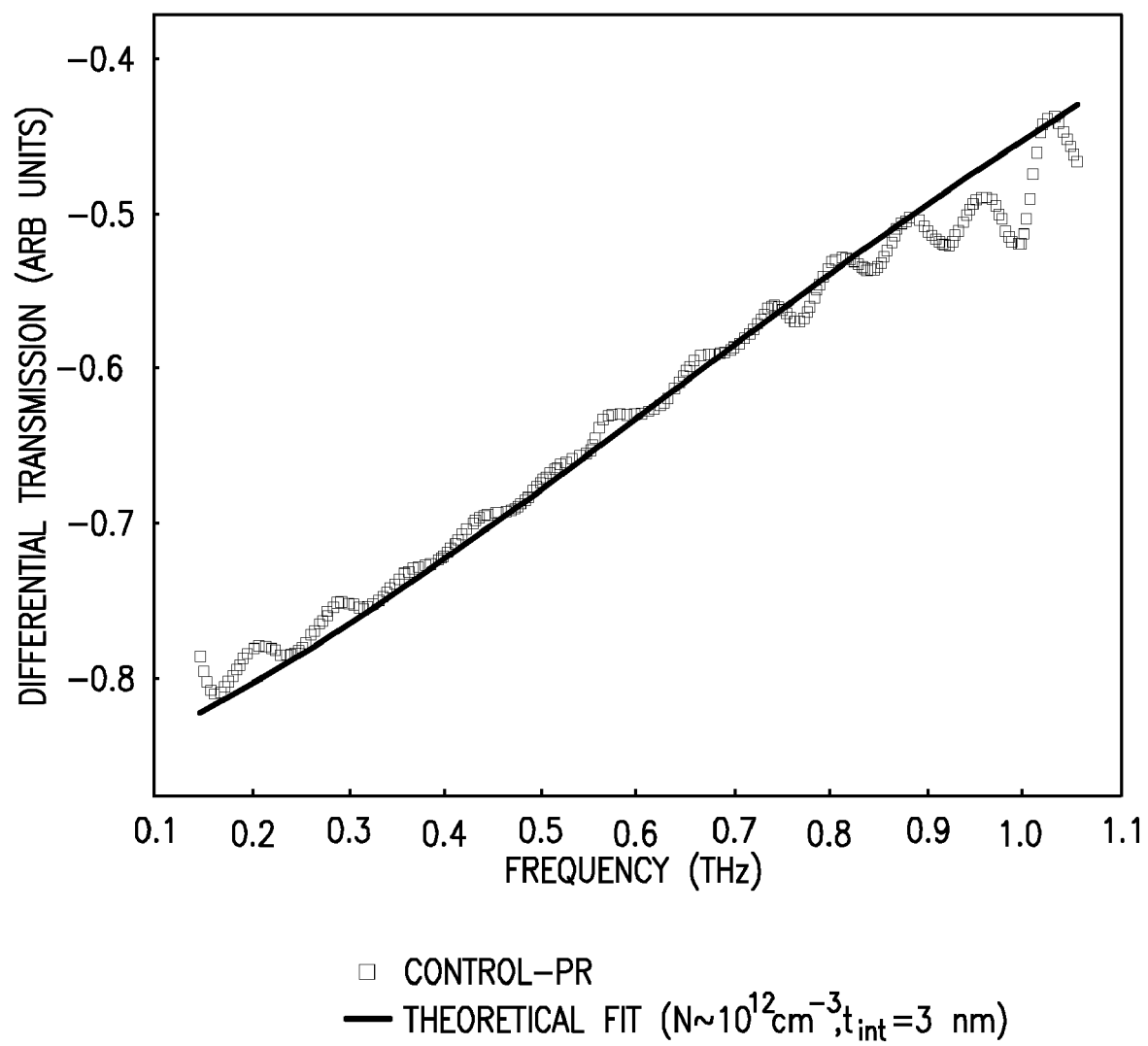
FIG. 19E is a graph of differential transmission versus frequency for a wafer in accordance with yet another embodiment of the present invention.
Figure 19F:
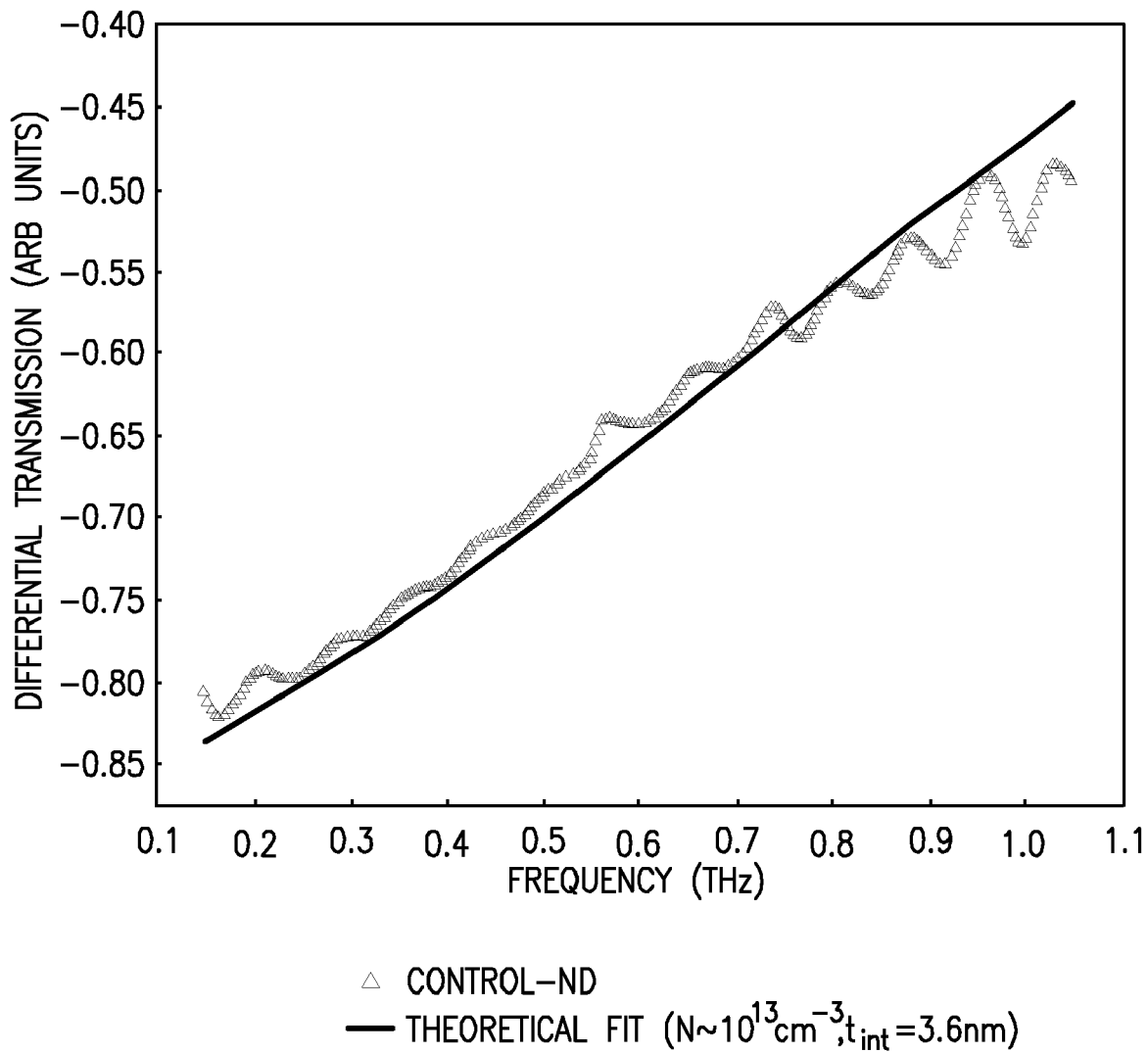
FIG. 19F is a graph of differential transmission versus frequency for a wafer in accordance with yet another embodiment of the present invention.

Finally, on applying the model as developed and described in the section "Advanced Modeling With Diffusion And Effective Medium Approximation," it is seen that the incorporation of diffusive effects and the BG effective medium approximation, the most accurate results are obtained because the effect of diffusion allows one to estimate the exact number of photoexcited defect states and since it has been assumed that the interfacial layer behaves as a Bruggeman effective medium with a mixture of Silicon dioxide and Hafnium dioxide it was also possible to estimate the thickness of the interfacial layer with a fair degree of accuracy. FIG. 19 shows the corresponding graphs for the different sets of wafers. FIG. 19 shows differential experimental measurements and corresponding theoretical-fit plots for wafers having various oxide layers and coatings. FIGS. 19A, 19C, and 19E show photoresist coated wafers indicated with the term "PR". FIGS. 19B, 19D, and D show $Si_3N_4$ coated wafers indicated with term "ND". The fitting parameters have been included in the legends of each of the FIGS for easy reference. It is seen that in all the cases, the thickness of the interfacial layer for ND-coated wafers is more than in the case of corresponding PR coated wafers. It is evident from the graphs that there is an excellent match of the theoretical model with the experimentally observed differential transmission. Table 4.4 lists the theoretical number of defect states and the thickness of the interfacial layer for each of the wafers. Interestingly, the results agree with the values obtained by electrical measurements as reported by other researchers working on similar structure wafers. See, Chau R. S., "Intel's breakthrough in High K gate dielectric drives Moore's law well into the future," Intel Technological Magazine, 1, 3-10 (2004); Muller D. A., Sorsch T., Moccio S., Baumann F. H., Evans-Lutterodt K. and Timp G., "The electronic structure at the atomic scale of ultrathin gate oxides," Nature, 399, 758-762 (1999); and Grunthaner F. J. and Grunthaner P. J., "Chemical and electronic structure of the $Si/SiO_2$ interface," Mater. Sci. Rep. 1, 65-160 (1986), each of which is fully incorporated herein by reference.

TABLE 4.4

Parameters of the Interface (Advanced Analysis)

| Gate Dielectric | No. of Defect States($cm^{-3}$) | Mobility ($cm^2$/V-s) | Interfacial layer thickness(nm) |
|---|---|---|---|
| $SiO_2$(PR) | $2.5 \times 10^{10}$ | 450 | 0.8 |
| $SiO_2$(ND) | $3.0 \times 10^{10}$ | 430 | 1.0 |
| $HfO_2$(PR) | $5.5 \times 10^{12}$ | 240 | 1.4 |
| $HfO_2$(ND) | $8.0 \times 10^{12}$ | 210 | 1.7 |

In accordance with the present invention, an all-optical non-contact technique is provided to estimate the number of defect states and the thickness of the interfacial layer for a stacked dielectric structure. The dielectrics studied are the present day industry standard, $SiO_2$, and the most promising replacement candidate of the future, $HfO_2$. It was observed that photoresist coated samples are more transmittive to THz radiation than the corresponding $Si_3N_4$ coated samples. This is probably due to the fact that photoresist is more absorptive to visible wavelengths than $Si_3N_4$.

The results obtained show THz spectroscopy can be employed to study the properties of "buried" layers for in-situ monitoring of the quality of the fabricated wafers, semiconductor metrology applications and other applications.

While the foregoing is directed to embodiments of the present invention, other and further embodiments of the invention may be devised without departing from the basic scope thereof, and the scope thereof is determined by the claims that follow.

All references cited herein are incorporated fully by reference. The following references are also hereby incorporated fully by reference:

"Optical properties of Silicon." Site details optical properties of Silicon at different wavelengths. Retrieved Feb. 17, 2006 from http://www.virginiasemi.com/pdf/Optical20Properties20 of 20Silicon 71502.pdf Abrahamson J., "Modeling Alternative High Dielectric Constant Thin Films," REU 2004 Summer Program, Advanced Materials Research Laboratory, University of Illinois at Chicago (2004).

Lee B. J. and Zhang B. M., "Development of experimentally validated optical property models for silicon and related materials," Proc. Of 11th IEEE International Conference on Advanced Thermal Processing of Semiconductors," RTP 2003, 143-150 (2003).

Semiconductor International, Reed Electronics Group. Site details properties of deep UV photoresist under different conditions. Retrieved Oct. 31, 2004 from http://www.reed-electronics.com/semiconductor/article/CA41503.pdf Perera A. G. U, Shen W. Z., Mallard W. C., Tanner M. O. and Wang K. L., "Far infrared free hole absorption in epitaxial silicon films for homojunction detectors," Appl. Phys. Lett., 71, 515-517 (1997).

Zukic M., Torr D. G., Span J. F. and Torr M. R., "Vacuum ultraviolet thin films. 1: Optical Constants of HaFBaF$_2$, CaF$_2$, LaF$_3$, MgF$_2$, Al$_2$O$_3$, HfO$_2$ and SiO$_2$ thin films," Appl. Opt., 29, 4284 (1990).

The invention claimed is:

1. A method for identifying a desired characteristic of an object, the method comprising the steps of:
   illuminating the object with continuous wave laser pump beam at a predetermined wavelength related to the desired characteristic, wherein the object includes a high-K dielectric material within the object;
   transmitting terahertz pulses at the object; and
   receiving terahertz pulses reflected by the object, so that the desired characteristic can be determined from the received terahertz pulses wherein the desired characteristic is a quantitative estimate of he one of defect density and mobility.

2. The method defined in claim 1 further including the step of measuring amplitude and phase components of the terahertz pulses received to generate first results.

3. The method defined in claim 2 further including the step of comparing the first results from the measuring step with second results to identify the desired characteristic, wherein the second results include amplitude and phase components of terahertz pulses received by reflection from the object in the absence of any continuous wave laser pump beam illumination.

4. The method as defined in claim 2 further including the steps of:
   generating second results by:
      transmitting second terahertz pulses at the object;
      receiving second terahertz pulses reflected by the object; and
      measuring amplitude and phase components of the second terahertz pulses received in the absence of any continuous wave laser pump beam illumination; and
   comparing the first results from the measuring step with second results to identify the desired characteristic.

5. The method as defined in claim 4 wherein the desired characteristic is defect density.

6. A method for identifying a desired characteristic of an object, the method comprising the steps of:
   illuminating the object with continuous wave laser pump beam at a predetermined wavelength related to the desired characteristic, wherein the object includes high-k dielectric material buried within the object;
   transmitting terahertz pulses at the object; and
   receiving the terahertz pulses transmitted through the object, so that the desired characteristic can be determined from the received terahertz pulses wherein the desired characteristic is a quantitative estimate of one of defect density and mobility.

7. The method defined in claim 6 further including the step of measuring amplitude and phase components of the terahertz pulses received to generate first results.

8. The method defined in claim 7 further including the step of comparing the first results from the measuring step with second results to identify the desired characteristic, wherein the second results include amplitude and phase components of terahertz pulses received by reflection from the object in the absence of any continuous wave laser pump beam illumination.

9. The method as defined in claim 8 wherein the desired characteristic is defect density.

10. The method as defined in claim 7 further including the steps of:
    generating second results by:
       transmitting second terahertz pulses at the object;
       receiving the second terahertz pulses transmitted through the object; and
       measuring amplitude and phase components of the second terahertz pulses
       received in the absence of any continuous wave laser pump beam illumination;
    comparing the first results from the measuring step with second results to identify the desired characteristic.

11. A method, comprising:
    providing a wafer including a crystal substrate and a high-K oxide dielectric layer disposed on the substrate;
    illuminating the wafer with a continuous wave laser pump beam;
    transmitting terahertz pulses at the wafer; and
    receiving terahertz pulses reflected by the wafer, or transmitted through the wafer, and quantitatively measuring at least one characteristic of the wafer at an interracial layer within the wafer.

12. The method of claim 11 wherein the crystal substrate is silicon and the dielectric layer is hafnium dioxide.

13. The method of claim 11 wherein the measuring step comprises:
    obtaining a numerical estimate of a defect density level at a dielectric layer within the wafer.

14. The method of claim 11 wherein the measuring step comprises:
    measuring a defect density level at an interface between the dielectric layer and the crystal substrate.

15. The method of claim 11 wherein the measuring step comprises:
    measuring defects in the dielectric layer immediately after growth of the dielectric layer.

16. The method of claim 11 wherein the measuring step comprises:
    using impedance matching to obtain a numerical estimate of a number of defect states at a buried dielectric layer within the wafer.

17. The method of claim 11 wherein the measuring step comprises:
    measuring defects at an interface between the crystal substrate and the dielectric layer.

18. The method of claim 11 further comprising:
    coating the wafer with one of photoresist and Si$_3$N$_4$.

19. The method of claim 11 wherein the measuring step comprises:
    measuring electron mobility in the crystal substrate.

* * * * *